(12) United States Patent
Videback

(10) Patent No.: US 8,597,206 B2
(45) Date of Patent: Dec. 3, 2013

(54) BIOPSY PROBE ASSEMBLY HAVING A MECHANISM TO PREVENT MISALIGNMENT OF COMPONENTS PRIOR TO INSTALLATION

(75) Inventor: Karsten Videback, Jyllinge (DK)

(73) Assignee: Bard Peripheral Vascular, Inc., Tempe, AZ (US)

( * ) Notice: Subject to any disclaimer, the term of this patent is extended or adjusted under 35 U.S.C. 154(b) by 834 days.

(21) Appl. No.: 12/577,300

(22) Filed: Oct. 12, 2009

(65) Prior Publication Data

US 2011/0087131 A1 Apr. 14, 2011

(51) Int. Cl.
*A61B 10/00* (2006.01)
(52) U.S. Cl.
USPC .................. 600/567; 606/167; 606/185
(58) Field of Classification Search
USPC .......... 600/562–568; 606/167, 170, 176, 179, 606/180, 184, 185
See application file for complete search history.

(56) References Cited

U.S. PATENT DOCUMENTS

| | | | |
|---|---|---|---|
| 737,293 A | 8/1903 | Summerfeldt |
| 1,585,934 A | 5/1926 | Muir |
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,289,669 A | 12/1966 | Dwyer et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,800,783 A | 4/1974 | Jamshidi |
| 3,844,272 A | 10/1974 | Banko |
| 3,882,849 A | 5/1975 | Jamshidi |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |

(Continued)

FOREIGN PATENT DOCUMENTS

| | | |
|---|---|---|
| DE | 3924291 A1 | 1/1991 |
| DE | 4041614 C1 | 10/1992 |

(Continued)

*Primary Examiner* — Max Hindenburg
*Assistant Examiner* — Renee Danega

(57) ABSTRACT

A biopsy probe assembly is configured for installation on a driver assembly. The biopsy probe assembly includes a plurality of components, each of the plurality of components being movable relative to another of the plurality of components, and each of the plurality of movable components having a respective alignment feature, wherein collectively the biopsy probe assembly has a plurality of alignment features. The plurality of alignment features of the plurality of components is aligned to form a continuous passage. A safety alignment pin is inserted into the continuous passage so as to lock relative positions of the plurality of components.

5 Claims, 19 Drawing Sheets

(56) References Cited

U.S. PATENT DOCUMENTS

| | | |
|---|---|---|
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,706,687 A | 11/1987 | Rogers |
| 4,776,346 A | 10/1988 | Beraha et al. |
| 4,844,087 A | 7/1989 | Garg |
| 4,850,354 A | 7/1989 | McGurk-Burleson et al. |
| 4,893,635 A | 1/1990 | de Groot et al. |
| 4,907,598 A | 3/1990 | Bauer |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,057,822 A | 10/1991 | Hoffman |
| 5,125,413 A | 6/1992 | Baran |
| 5,138,245 A | 8/1992 | Mattinger et al. |
| 5,146,921 A | 9/1992 | Terwilliger et al. |
| 5,158,528 A | 10/1992 | Walker et al. |
| 5,176,628 A | 1/1993 | Charles et al. |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,282,476 A | 2/1994 | Terwilliger |
| 5,282,477 A | 2/1994 | Bauer |
| 5,324,306 A | 6/1994 | Makower et al. |
| 5,334,183 A | 8/1994 | Wuchinich |
| 5,368,029 A | 11/1994 | Holcombe et al. |
| 5,368,045 A | 11/1994 | Clement et al. |
| 5,383,874 A | 1/1995 | Jackson et al. |
| 5,400,798 A | 3/1995 | Baran |
| 5,439,474 A | 8/1995 | Li |
| 5,458,112 A | 10/1995 | Weaver |
| 5,469,860 A | 11/1995 | De Santis |
| 5,479,486 A | 12/1995 | Saji |
| 5,485,917 A | 1/1996 | Early |
| 5,492,130 A | 2/1996 | Chiou |
| 5,496,860 A | 3/1996 | Matsumoto et al. |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,554,151 A | 9/1996 | Hinchliffe |
| 5,560,373 A | 10/1996 | DeSantis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,585 A | 2/1997 | Banik et al. |
| 5,602,449 A | 2/1997 | Krause et al. |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregorie et al. |
| 5,951,490 A | 9/1999 | Fowler |
| 5,951,575 A | 9/1999 | Bolduc et al. |
| 5,964,716 A | 10/1999 | Gregorie et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,036,657 A | 3/2000 | Milliman et al. |
| 6,050,955 A | 4/2000 | Bryan et al. |
| 6,055,870 A | 5/2000 | Jaeger |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 * | 8/2002 | Viola et al. .................... 600/562 |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |

(56) References Cited

U.S. PATENT DOCUMENTS

| | | |
|---|---|---|
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,010,332 B1 | 3/2006 | Irvin et al. |
| 7,025,732 B2 | 4/2006 | Thompson et al. |
| D525,583 S | 7/2006 | Vu |
| 7,153,274 B2 | 12/2006 | Stephens et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hlbner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,432,813 B2 | 10/2008 | Postma |
| 7,452,367 B2 | 11/2008 | Rassman et al. |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,762,961 B2 | 7/2010 | Heske et al. |
| 7,828,746 B2 | 11/2010 | Teague |
| 7,854,706 B2 | 12/2010 | Hibner |
| 7,883,476 B2 | 2/2011 | Miller et al. |
| 7,974,681 B2 | 7/2011 | Wallace et al. |
| 8,073,008 B2 | 12/2011 | Mehta et al. |
| 8,190,238 B2 | 5/2012 | Moll et al. |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0120212 A1 | 8/2002 | Ritchart et al. |
| 2002/0156395 A1 | 10/2002 | Stephens et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0049128 A1 | 3/2004 | Miller et al. |
| 2004/0054299 A1 | 3/2004 | Burdorff et al. |
| 2004/0082915 A1 | 4/2004 | Kadan |
| 2004/0092992 A1 | 5/2004 | Adams et al. |
| 2004/0186393 A1 | 9/2004 | Leigh et al. |
| 2004/0210161 A1 | 10/2004 | Burdorff et al. |
| 2004/0215103 A1 | 10/2004 | Mueller, Jr. et al. |
| 2004/0220495 A1 | 11/2004 | Cahir et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0080355 A1 | 4/2005 | Mark |
| 2005/0085838 A1 | 4/2005 | Thompson et al. |
| 2005/0088120 A1 | 4/2005 | Avis |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0275378 A1 | 12/2005 | Canino et al. |
| 2005/0277829 A1 | 12/2005 | Tsonton et al. |
| 2005/0277871 A1 | 12/2005 | Selis |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258956 A1 | 11/2006 | Haberstich et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 | 5/2007 | Stephens et al. |
| 2007/0118049 A1 | 5/2007 | Viola |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0179401 A1 | 8/2007 | Hibner |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |

(56) References Cited

U.S. PATENT DOCUMENTS

| | | |
|---|---|---|
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1* | 3/2008 | Reuber et al. ............. 600/567 |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0214955 A1 | 9/2008 | Speeg et al. |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0030405 A1 | 1/2009 | Quick et al. |
| 2009/0062624 A1 | 3/2009 | Neville |
| 2009/0082695 A1 | 3/2009 | Whitehead |
| 2009/0125062 A1 | 5/2009 | Arnin |
| 2009/0137927 A1 | 5/2009 | Miller |
| 2009/0171243 A1 | 7/2009 | Hibner et al. |
| 2009/0227893 A1 | 9/2009 | Coonahan et al. |
| 2010/0030020 A1 | 2/2010 | Sanders et al. |
| 2010/0030108 A1 | 2/2010 | Anderson et al. |
| 2010/0063416 A1 | 3/2010 | Cicenas et al. |
| 2010/0106053 A1 | 4/2010 | Videbaek et al. |
| 2010/0152611 A1 | 6/2010 | Parihar et al. |
| 2010/0160820 A1 | 6/2010 | Weikel, Jr. et al. |
| 2010/0210966 A1 | 8/2010 | Videbaek |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2011/0054350 A1 | 3/2011 | Videbaek |
| 2011/0077551 A1 | 3/2011 | Videbaek |
| 2011/0105945 A1 | 5/2011 | Videbaek et al. |
| 2011/0105946 A1 | 5/2011 | Sorensen et al. |
| 2011/0152715 A1 | 6/2011 | Delap et al. |
| 2011/0160611 A1 | 6/2011 | Ritchart et al. |

FOREIGN PATENT DOCUMENTS

| | | |
|---|---|---|
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1665989 A2 | 6/2006 |
| EP | 2095772 A1 | 9/2009 |
| EP | 2106750 A2 | 10/2009 |
| FR | 1345429 A | 12/1963 |
| FR | 2739293 A1 | 4/1997 |
| GB | 2018601 A | 10/1979 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9624289 A2 | 8/1996 |
| WO | 9628097 A1 | 9/1996 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008024684 A2 | 2/2008 |
| WO | 2008040812 A1 | 4/2008 |
| WO | 2008131362 A2 | 10/2008 |
| WO | 2010107424 A1 | 9/2010 |
| WO | 2010120294 A1 | 10/2010 |
| WO | 2011019343 A1 | 2/2011 |

* cited by examiner

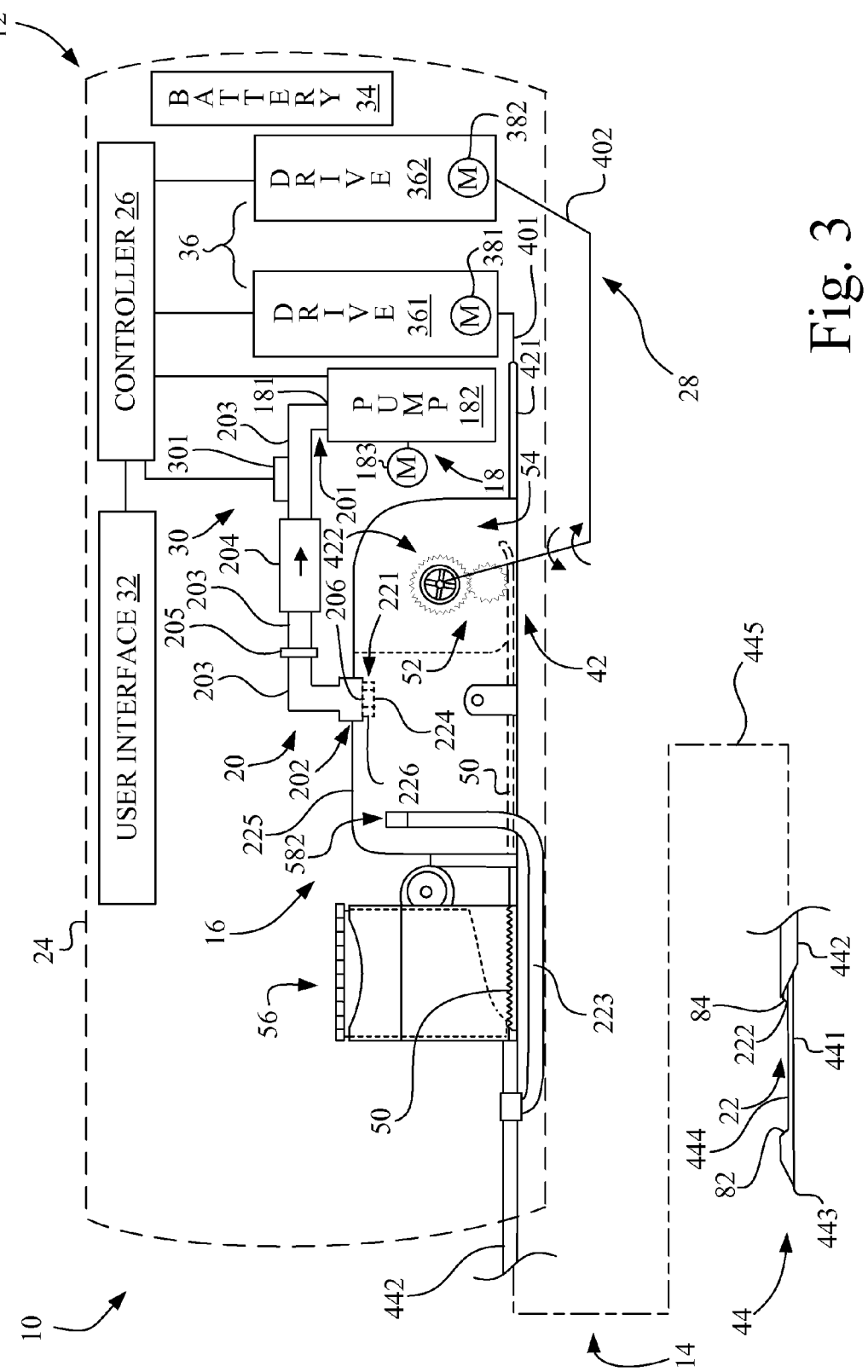

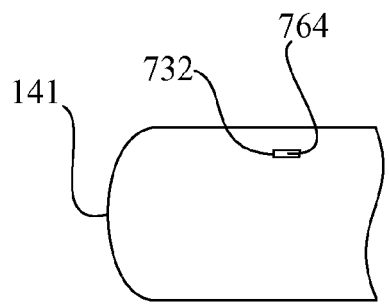
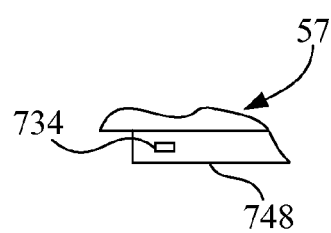
Fig. 22A        Fig. 22B
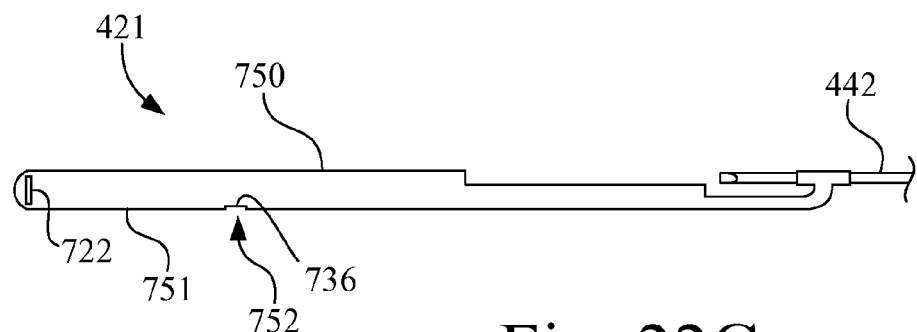
Fig. 22C
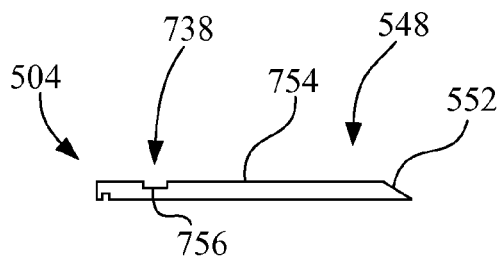
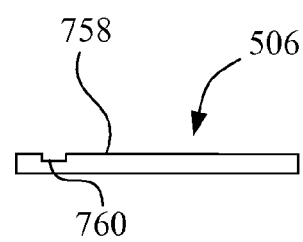
Fig. 22D        Fig. 22E
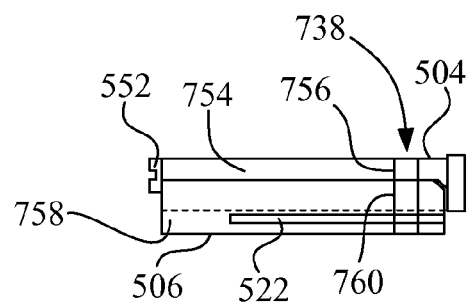
Fig. 22F

BIOPSY PROBE ASSEMBLY HAVING A MECHANISM TO PREVENT MISALIGNMENT OF COMPONENTS PRIOR TO INSTALLATION

CROSS-REFERENCE TO RELATED APPLICATIONS

This application is related to International Application No. PCT/US2009/040663, filed Apr. 15, 2009, and U.S. patent application Ser. No. 12/551,819 filed Sep. 1, 2009.

MICROFICHE APPENDIX

None.

GOVERNMENT RIGHTS IN PATENT

None.

BACKGROUND OF THE INVENTION

1. Field of the Invention

The present invention relates to a biopsy apparatus, and, more particularly, to a biopsy probe assembly having a mechanism to prevent misalignment of components of the biopsy probe assembly prior to installation, so as to aid in the proper mounting of the biopsy probe assembly to the driver assembly of a biopsy apparatus.

2. Description of the Related Art

A biopsy may be performed on a patient to help in determining whether the cells in a biopsied region are cancerous. One type of vacuum assisted biopsy apparatus includes a hand-held driver assembly having a vacuum source, and a disposable biopsy probe assembly configured for releasable attachment to the driver assembly. One biopsy technique used to evaluate breast tissue, for example, involves inserting a biopsy probe into the breast tissue region of interest to capture one or more tissue samples from the region.

The biopsy probe typically includes a biopsy cannula, e.g., a needle, having a cylindrical side wall defining a lumen, and having a side sample notch located near the distal end that extends though the side wall to the lumen. A cutting cannula is positioned coaxial with the biopsy cannula to selectively open and close the sample notch. Vacuum is applied to the lumen, and in turn to the sample notch, for receiving the tissue to be sampled when the sample notch is opened, after which the sample notch is closed by the cutting cannula to sever the tissue, and the severed tissue is transported by vacuum out of the lumen and collected.

To insure proper operation of the biopsy apparatus, the biopsy probe must be properly mounted to the driver assembly, with the various mechanical drive components of the driver assembly being properly engaged with the various mechanical driven components of the biopsy probe.

SUMMARY OF THE INVENTION

The present invention provides a biopsy probe assembly having a mechanism to prevent misalignment of components of the biopsy probe assembly prior to and during installation of the biopsy probe assembly on the driver assembly, so as to aid in the proper mounting of the biopsy probe assembly to the driver assembly of a biopsy apparatus.

As used herein, the terms "first" and "second" preceding an element name, e.g., first alignment feature, second alignment feature, third alignment feature, etc., are for identification purposes to distinguish between different elements having similar characteristic, and are not intended to necessarily imply order, unless otherwise specified, nor are the terms "first", "second", etc., intended to preclude the inclusion of additional similar elements.

The invention, in one form thereof, is directed to a biopsy probe assembly configured for installation on a driver assembly. The biopsy probe assembly includes a housing, and a biopsy probe having a cannula arranged along a longitudinal axis. A sample basket is arranged coaxially with the cannula. A cannula driver is coupled to the housing. The cannula driver is connected to the cannula to facilitate movement of the cannula along the longitudinal axis. A driven unit is contained at least in part in the housing. The driven unit is coupled to the sample basket to facilitate movement of the sample basket relative to the longitudinal axis. A slider assembly has a slider driver and a slider that are movable to selectively couple the cannula driver to the driven unit in a piercing shot mode and to decouple the cannula driver from the driven unit in a tissue harvesting mode. A cover is movably coupled to the housing. A plurality of alignment features is provided, each alignment feature being associated with a respective one of the cannula driver, the slider assembly and the cover. The plurality of alignment features when aligned form a continuous passage. A safety alignment pin is positioned in the continuous passage to engage each of the plurality of alignment features to prevent relative movement of the cannula driver, the slider driver and the cover prior to installation of the biopsy probe assembly on the driver assembly.

The invention, in another form thereof, is directed to a biopsy probe assembly configured for installation on a driver assembly. The biopsy probe assembly includes a biopsy probe having a cannula arranged along a longitudinal axis. A cover has a first alignment feature. A housing is slidably coupled to the cover. The housing has a second alignment feature. A first driven unit is slidably coupled to the housing. The first driven unit has a third alignment feature. The first driven unit is connected to the cannula to facilitate movement of the cannula along the longitudinal axis. An alignment pin is configured to facilitate concurrent engagement with each of the first alignment feature, the second alignment feature, and the third alignment feature so as to lock relative positions of the cover, the housing, and the first driven unit.

The invention, in another form thereof, is directed to a biopsy probe assembly configured for installation on a driver assembly. The biopsy probe assembly includes a biopsy probe having a sample basket arranged coaxially with a cutter cannula along a longitudinal axis. A cover has a first alignment feature. A housing is slidably coupled to the cover. The housing has a second alignment feature. A cannula driver has a third alignment feature. The cannula driver is slidably coupled to the housing. The cannula driver is connected to the cutter cannula to facilitate movement of the cutter cannula along the longitudinal axis. A flexible toothed rack is connected to the sample basket to facilitate movement of the sample basket along the longitudinal axis. A gear train is contained in the housing. The gear train includes a clutch drive configured to selectively drivably couple the gear train to the flexible toothed rack. A pivot member is pivotably coupled to the cannula driver. The pivot member provides selectable coupling between the cannula driver and the flexible toothed rack. A slider assembly is coupled to the pivot member to operate the pivot member to facilitate the selectable coupling between the cannula driver and the flexible toothed rack via the pivot member. The slider assembly is further configured to selectively engage the clutch drive. The slider assembly includes a slider driver movable between an extended position and a retracted position. The retracted position of the slider driver effects an engagement of the clutch drive and disengagement between the cannula driver and the flexible toothed drive. The extended position of the slider driver effects a disengagement of the clutch drive and an engagement between the cannula driver and the flexible toothed drive. The slider driver has a fourth alignment feature. An alignment pin is configured to facilitate manual concurrent engagement with each of the first alignment feature, the second alignment feature, the third alignment feature and the fourth alignment feature so as to lock relative positions of the cover, the housing, the cannula driver and the slider driver.

The invention, in another form thereof, is directed to a biopsy apparatus including a driver assembly and a biopsy probe assembly. The driver assembly has a first drive and a controller communicatively coupled to the first drive. The controller executes program instructions to preposition the first drive to an initialized state. A biopsy probe assembly is configured for releasable attachment to the driver assembly after the driver assembly is placed in the initialized state. The biopsy probe assembly includes a biopsy probe having a cannula arranged along a longitudinal axis. A cover has a first alignment feature. A housing is slidably coupled to the cover. The housing has a second alignment feature. A first driven unit is movably coupled to the housing. The first driven unit is configured for drivable coupling to the first drive of the driver assembly. The first driven unit has a third alignment feature. The first driven unit is connected to the cannula to facilitate movement of the cannula along the longitudinal axis. An alignment pin is configured to facilitate concurrent engagement with each of the first alignment feature, the second alignment feature and the third alignment feature so as to lock relative positions of the cover, the housing and the first driven unit.

The invention, in another form thereof, is directed to a biopsy probe assembly configured for installation on a driver assembly. The biopsy probe assembly includes a plurality of components, each of the plurality of components being movable relative to another of the plurality of components, and each of the plurality of movable components having a respective alignment feature, wherein collectively the biopsy probe assembly has a plurality of alignment features. The plurality of alignment features of the plurality of components is aligned to form a continuous passage. A safety alignment pin is inserted into the continuous passage so as to lock relative positions of the plurality of components.

The invention, in another form thereof, is directed to a method for installing a biopsy probe assembly on a driver assembly to form a biopsy apparatus. The method includes prepositioning a drive of the driver assembly to an initialized state; providing the biopsy probe assembly configured for installation on the driver assembly, the biopsy probe assembly including a biopsy probe having a cannula arranged along a longitudinal axis coaxially with a sample basket, a cover having a first alignment feature, a housing slidably coupled to the cover, the housing having a second alignment feature, and a driven unit slidably coupled to the housing, the driven unit having a third alignment feature, the driven unit being connected to the cannula to facilitate movement of the cannula along the longitudinal axis, wherein the first alignment feature, the second alignment feature and the third alignment feature are aligned to form a continuous passage, with an alignment pin being received in the continuous passage to lock relative positions of the cover, the housing and the driven unit; seating at least a portion of the biopsy probe assembly in an elongate cavity of the driver assembly, with the drive drivably engaging the driven unit; after the seating, removing the alignment pin to unlock the cover, the housing, and the driven unit; and after the alignment pin is removed, sliding the cover relative to the housing to latch the biopsy probe assembly to the driver assembly.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 3 is a schematic representation of the biopsy apparatus of FIG. 1;

FIG. 22A is a bottom view of a portion of the cover of the biopsy probe assembly of FIG. 20, which includes a cover alignment feature;

FIG. 22B is a top view of a portion of the housing of the biopsy probe assembly of FIG. 20, which includes a housing alignment feature;

FIG. 22C is a top view of a portion of the first driven unit (cannula driver) of the biopsy probe assembly of FIG. 20, which includes a cannula driver alignment feature;

FIG. 22D is a top view of the slider driver illustrated in FIG. 15A, which includes a slider driver alignment feature;

FIG. 22E is a top view of the slider illustrated in FIG. 15A; and

FIG. 22F is an opposite side view of the slider driver and slider illustrated in FIG. 15A.

Corresponding reference characters indicate corresponding parts throughout the several views. The exemplifications set out herein illustrate an embodiment of the invention, and such exemplifications are not to be construed as limiting the scope of the invention in any manner.

DETAILED DESCRIPTION OF THE INVENTION

Figure 1:
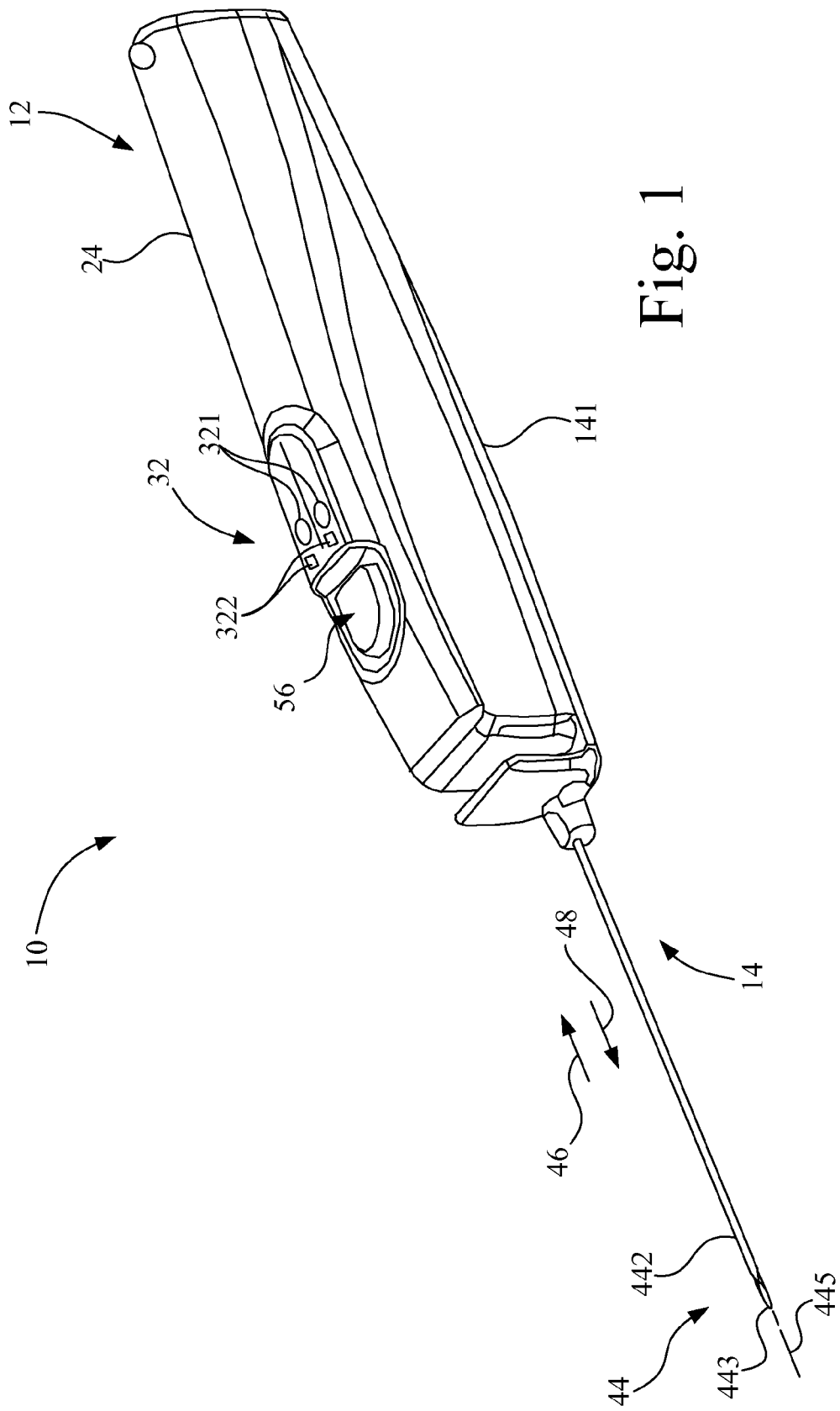
FIG. 1 is a perspective view of a biopsy apparatus, configured in accordance with an embodiment of the present invention, with a disposable biopsy probe mounted to a driver assembly.
Figure 2:
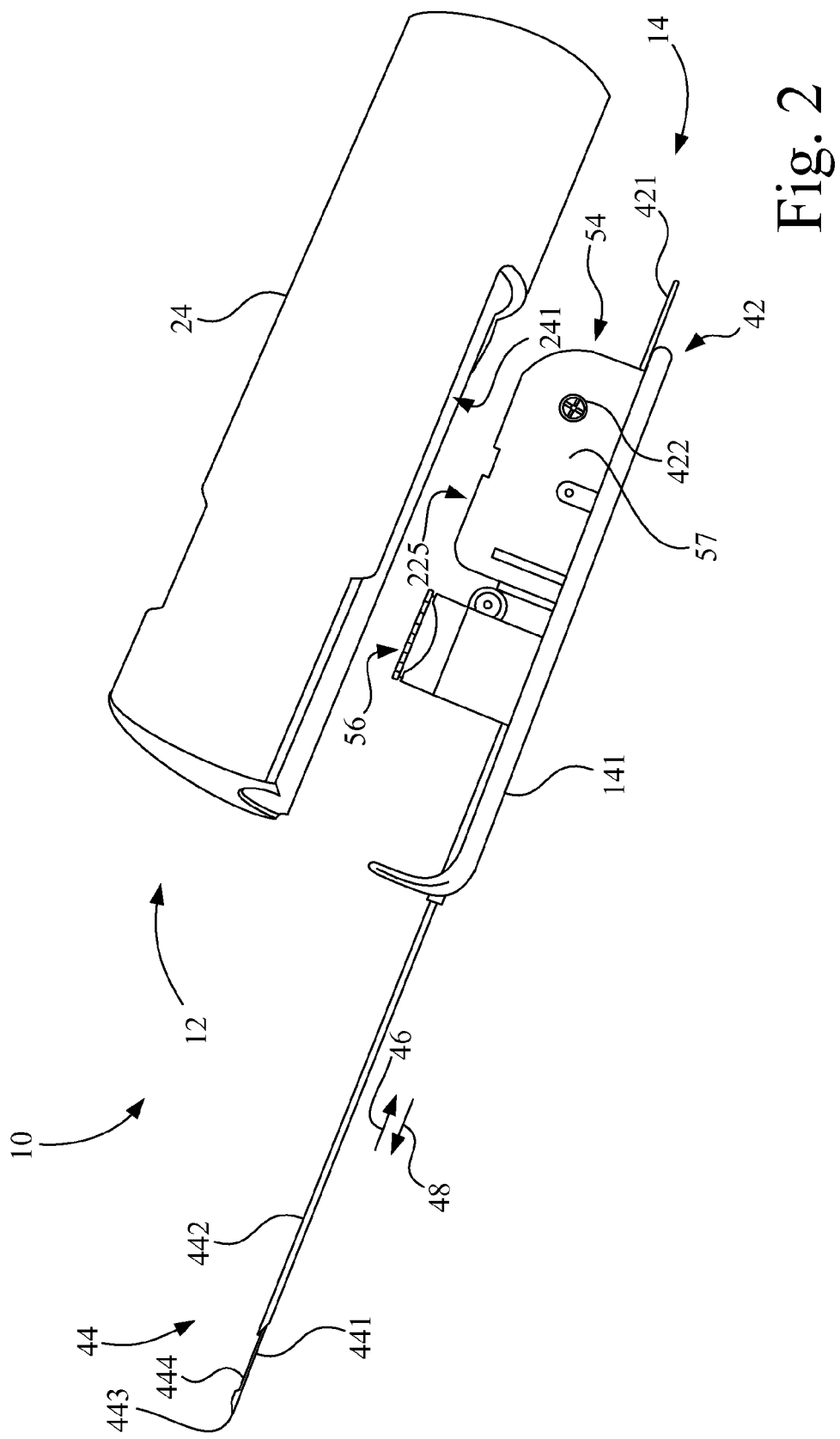
FIG. 2 is a perspective view of a biopsy apparatus of FIG. 1, with the disposable biopsy probe detached from the driver assembly.

Referring now to the drawings, and more particularly to FIGS. 1 and 2, there is shown a biopsy apparatus 10 which generally includes a non-invasive, e.g., non-disposable, driver assembly 12 and a disposable biopsy probe assembly 14.

Referring also to FIG. 3, driver assembly 12 and disposable biopsy probe assembly 14 collectively include a fluid management system 16 that includes a vacuum source 18, first vacuum path 20 and a second vacuum path 22. Vacuum source 18 and a first vacuum path 20 are permanently associated with driver assembly 12, and a second vacuum path 22 is permanently associated with disposable biopsy probe assembly 14, as more fully described below, to help facilitate the safe and effective collection of a biopsy tissue sample.

As used herein, the term "non-disposable" is used to refer to a device that is intended for use on multiple patients during the lifetime of the device, and the term "disposable" is used to refer to a device that is intended to be disposed of after use on a single patient. Also, the term "vacuum path" means a fluid passageway used to facilitate a vacuum between two points, the fluid passageway passing through one or more components, such as for example, one or more of tubing, conduits, couplers, and interposed devices. Also, the term "permanently associated" means a connection that is not intended for releasable attachment on a routine basis during the lifetime of the components. Thus, for example, driver assembly 12 including vacuum source 18 and first vacuum path 20 is reusable as a unit in its entirety, whereas disposable biopsy probe assembly 14 and second vacuum path 22 are disposable as a unit in its entirety.

Driver assembly 12 includes a housing 24 configured, and ergonomically designed, to be grasped by a user. Driver assembly 12 includes (contained within housing 24) vacuum source 18, first vacuum path 20, a controller 26, an electromechanical power source 28, and a vacuum monitoring mechanism 30. A user interface 32 is located to be mounted to, and externally accessible with respect to, housing 24. Housing 24 defines an elongate cavity 241 which is configured for receiving a corresponding housing 57 of biopsy probe assembly 14 when driver assembly 12 is mounted to biopsy probe assembly 14.

Controller 26 is communicatively coupled to electromechanical power source 28, vacuum source 18, user interface 32, and vacuum monitoring mechanism 30. Controller 26 may include, for example, a microprocessor and associated memory for executing program instructions to perform functions associated with the retrieval of biopsy tissue samples, such as controlling one or more components of vacuum source 18 and electromechanical power source 28. Controller 26 also may execute program instructions to monitor one or more conditions and/or positions of components of biopsy apparatus 10, and to monitor the status of fluid management system 16 associated with driver assembly 12 and biopsy probe assembly 14.

The user interface 32 includes control buttons 321 and visual indicators 322, with control buttons 321 providing user control over various functions of biopsy apparatus 10, and visual indicators 322 providing visual feedback of the status of one or more conditions and/or positions of components of biopsy apparatus 10.

The electromechanical power source 28 may include, for example, an electrical energy source, e.g., battery, 34 and an electrical drive assembly 36. Battery 34 may be, for example, a rechargeable battery. Battery 34 provides electrical power to all electrically powered components in biopsy apparatus 10, and thus for simplicity in the drawings, such electrical couplings are not shown. For example, battery 34 is electrically coupled to vacuum source 18, controller 26, user interface 32 and electrical drive assembly 36.

In the present embodiment, electrical drive assembly 36 includes a first drive 361 and a second drive 362, each being respectively coupled to battery 34, and each of first drive 361 and second drive 362 respectively electrically and controllably coupled to user interface 32.

First drive 361 may include an electrical motor 381 and a motion transfer unit 401 (shown schematically by a line). Second drive 362 may include an electrical motor 382 and a motion transfer unit 402 (shown schematically by a line). Each electrical motor 381, 382 may be, for example, a direct current (DC) motor, stepper motor, etc. Motion transfer unit 401 of first drive 361 may be configured, for example, with a rotational-to-linear motion converter, such as a worm gear arrangement, rack and pinion arrangement, etc., or a solenoid-slide arrangement, etc. Motion transfer unit 402 of second drive 362 may be configured to transmit rotary motion. Each of first drive 361 and second drive 362 may include one or more of a gear, gear train, belt/pulley arrangement, etc.

Vacuum source 18 is electrically coupled to battery 34, and has a vacuum source port 181 for establishing a vacuum. Vacuum source 18 is electrically and controllably coupled to user interface 32. Vacuum source 18 may further include, for example, a vacuum pump 182 driven by an electric motor 183. Vacuum pump 182 may be, for example, a peristaltic pump, a diaphragm pump, syringe-type pump, etc.

Figure 4A:
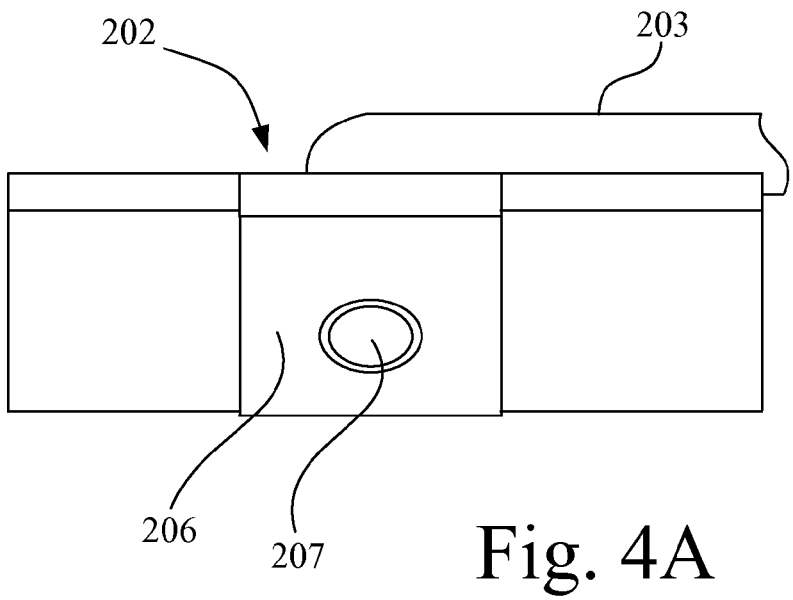
FIG. 4A is a perspective view of a vacuum seal element of the vacuum path of the driver assembly of FIG. 3.

First vacuum path 20 of driver assembly 12 is permanently associated with vacuum source 18. First vacuum path 20, also sometimes referred to as a non-disposable vacuum path, has a proximal end 201 and a distal end 202, and includes, for example, conduits 203, a first one-way valve 204, and a particulate filter 205. Proximal end 201 is fixedly coupled to vacuum source 18 in fluid communication therewith, e.g., is fixedly connected to vacuum source port 181 of vacuum source 18. Referring also to FIG. 4A, distal end 202 includes a first vacuum seal element 206. In the present embodiment, first vacuum seal element 206 is a planar abutment surface that surrounds a first passageway 207 of first vacuum path 20.

First one-way valve 204 is configured and arranged to permit a negative pressure fluid flow toward vacuum source 18 and to prevent a positive pressure fluid flow away from vacuum source 18 toward the distal end 202 of first vacuum path 20. The first one-way valve 204 may be, for example, a check-valve, such as a ball valve or reed valve, that opens with a fluid flow toward vacuum source 18, and closes in the case of a reverse (positive) flow away from vacuum source 18.

In the present embodiment, particulate filter 205 is located between vacuum source 18 and distal end 202 of first vacuum path 20. Particulate filter 205 may be, for example, a mesh screen formed from metal or plastic. However, it is contemplated that particulate filter 205 may be located in fluid management system 16 between vacuum source 18 and a vacuum receiving component of biopsy probe assembly 14.

The vacuum monitoring mechanism 30 is coupled to vacuum source 18 to shut off vacuum source 18 when a sensed vacuum level has fallen below a threshold level. Vacuum monitoring mechanism 30 may include, for example, a vacuum monitor and control program executing on controller 26, and a pressure sensor 301 coupled to controller 26, and in fluid communication with first vacuum path 20 for detecting a pressure in first vacuum path 20. If, for example, the vacuum flow level in first vacuum path 20 falls below a predetermined level, indicating a restriction in fluid management system 16, controller 26 may respond by shutting off vacuum source 18, e.g., turning off electric motor 183. Alternatively, controller 26 may monitor the current supplied to electric motor 183, and if the current exceeds a predetermined amount, indicating a restriction in fluid management system 16, controller 26 may respond by shutting off vacuum source 18, e.g., turning off electric motor 183.

The disposable biopsy probe assembly 14 is configured for releasable attachment to driver assembly 12. As used herein, the term "releasable attachment" means a configuration that facilitates an intended temporary connection followed by selective detachment involving a manipulation of disposable biopsy probe assembly 14 relative to driver assembly 12, without the need for tools.

The disposable biopsy probe assembly 14 includes a cover (frame) 141 to which a transmission device 42, a biopsy probe 44, housing 57 and the second vacuum path 22 are mounted, with housing 57 being slidably coupled to cover 141. The sliding coupling of housing 57 to cover 141 may be achieved, for example, by a rail and U-bracket configuration 14-1, illustrated schematically in FIG. 14. Cover 141 serves as a slidable cover to close elongate cavity 241 in housing 24 of driver assembly 12 to protect the internal structure of driver assembly 12 when biopsy probe assembly 14 is mounted to driver assembly 12. Biopsy probe 44 is drivably coupled to transmission device 42, and transmission device 42 is drivably coupled to electromechanical power source 28 of driver assembly 12 when biopsy probe assembly 14 is mounted to driver assembly 12.

In the embodiment shown, transmission device 42 includes a first driven unit 421 and a second driven unit 422 that are drivably engaged with various components of biopsy probe 44. Also, first driven unit 421 is drivably engaged with first drive 361 of electrical drive assembly 36 of driver assembly 12. Second driven unit 422 is drivably engaged with second drive 362 of electrical drive assembly 36 of driver assembly 12. First driven unit 421 is slidably coupled to housing 57, and second driven unit 422 is contained in housing 57. The sliding coupling of first driven unit 421 (e.g., a cannula driver) may be achieved by placing first driven unit 421 in a longitudinal slide channel 57-1 formed in housing 57 (FIG. 16).

In the embodiment shown (see, e.g., FIGS. 1-3), biopsy probe 44 includes a sample basket 441 and a cutter cannula 442. Sample basket 441 has a sharpened tip 443 to aid in puncturing tissue and has a sample notch 444 in the form of a recessed region for receiving a biopsy tissue sample. Sample basket 441 and a cutter cannula 442 are configured to be individually movable along a longitudinal axis 445.

In operation, cutter cannula 442 is linearly driven by first driven unit 421 to traverse over sample notch 444 of sample basket 441 along longitudinal axis 445. For example, first driven unit 421 may be in the form of a linear slide that is drivably engaged with first drive 361 of driver assembly 12, which in turn drives cutter cannula 442 along longitudinal axis 445 in a first direction 46, i.e., toward a proximal end of driver assembly 12, to expose sample notch 444 of sample basket 441, and drives cutter cannula 442 in a second direction 48 opposite to first direction 46 to sever tissue prolapsed into sample notch 444. Also, first driven unit 421 and second driven unit 422 may be configured to operate in unison to advance both sample basket 441 and cutter cannula 442 in unison along an longitudinal axis 445 in a piercing shot operation to aid in inserting biopsy probe 44 into fibrous tissue.

The second driven unit 422 may include a flexible toothed rack 50 and a gear train 52. Flexible toothed rack 50 is connected to sample basket 441, and a portion of gear train 52 is engaged with the teeth of flexible toothed rack 50. In operation, second drive 362 transfers rotary motion to gear train 52, and in turn gear train 52 engages flexible toothed rack 50 to move sample basket 441 linearly to transport the tissue captured in sample notch 444 out of the body of the patient. Flexible toothed rack 50 is received in a coiling unit 54 when retracting, thereby enabling substantial reduction in the overall device length of biopsy apparatus 10 as compared to a rigid capture system. Each harvested tissue sample is transported out of the body of the patient and is collected by tissue sample retrieval mechanism 56, which scoops the tissue sample out of sample notch 444.

In the present embodiment, coiling unit 54 and tissue sample retrieval mechanism 56 are as an integral unit with housing 57 that is common to coiling unit 54 and tissue sample retrieval mechanism 56. Housing 57 is attached, e.g., slidably coupled, to cover 141, and contains gear train 52 with at least a portion of flexible toothed rack 50 in engagement with gear train 52. Tissue sample retrieval mechanism 56 will be described in greater detail later. As shown, for example, in FIGS. 2, 5A and 6-8, housing 57 has a distinct shape S1 as a combination of curved and flat surfaces with an overall height H1, length L1, and width W1 dimensions which in combination define a unique profile of housing 57.

In the present embodiment, the second vacuum path 22, also sometimes referred to as a disposable vacuum path 22, has a first end 221 and a second end 222, and includes for example, conduits 223, a second one-way valve 224, and a fluid management tank 225. The first end 221 is configured for removable attachment to the distal end 202 of the first vacuum path 20 of driver assembly 12. The second end 222 is coupled in fluid communication with sample basket 441, and more particularly, is coupled in fluid communication with sample notch 444 of sample basket 441.

Figure 4B:
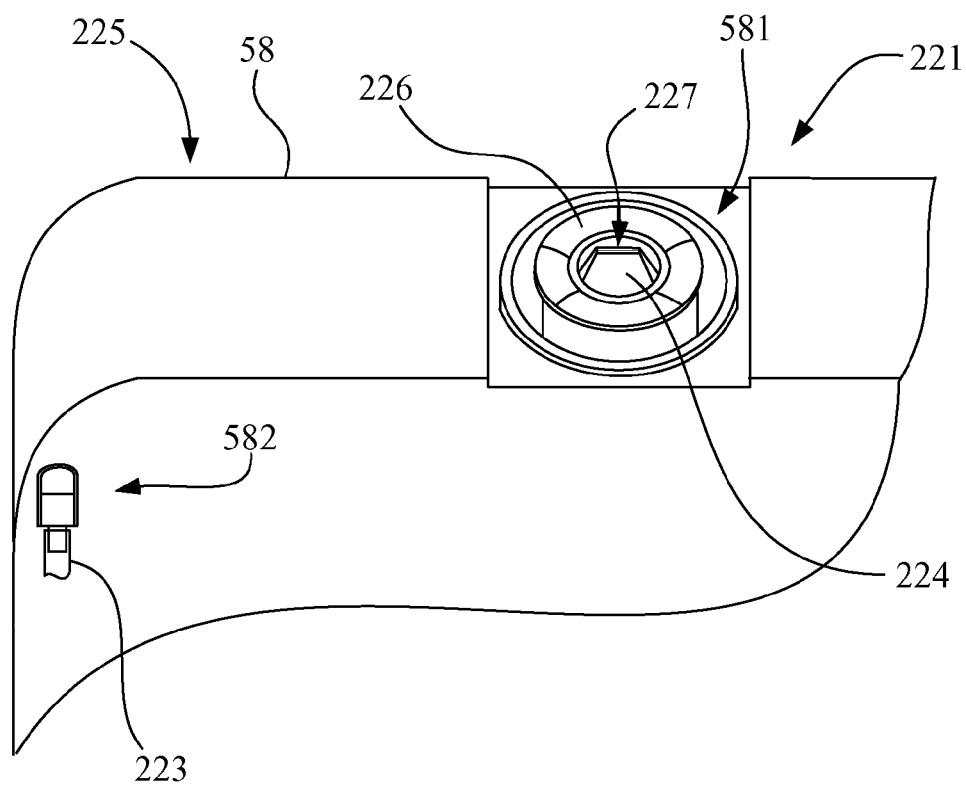
FIG. 4B is a perspective view of a vacuum seal element of the vacuum path of the disposable biopsy probe of FIG. 3.

Referring also to FIG. 4B, the first end 221 of the disposable vacuum path 22 includes a second vacuum seal element 226. The first vacuum seal element 206 of the driver assembly 12 contacts the second vacuum seal element 226 of the disposable biopsy probe assembly 14 in sealing engagement when the disposable biopsy probe assembly 14 is attached to driver assembly 12. The second vacuum seal element 226 is a compliant, e.g., rubber, annular member that surrounds a second passageway 227 of the second vacuum path 22.

The second one-way valve 224 configured and arranged to permit the negative pressure fluid flow from sample basket 441 toward the first end 221 of the second vacuum path 22, and to redundantly (in conjunction with first one-way valve 204 of driver assembly 12) prevent any positive pressure fluid flow in a direction from the first end 221 of the second vacuum path 22 toward sample basket 441. In other words, the second one-way valve 224 provides a redundant second level of protection in preventing any positive pressure from reaching sample notch 444 of sample basket 441. In the present embodiment, the second one-way valve 224 may be, for example, a duckbill valve, e.g., a reed-type valve, that opens with a fluid flow out the bill portion of the duckbill valve, and closes with a reverse flow. As shown, the second one-way valve 224 may be positioned within the second vacuum seal element 226 at first end 221 of second vacuum path 22.

Figure 5A:
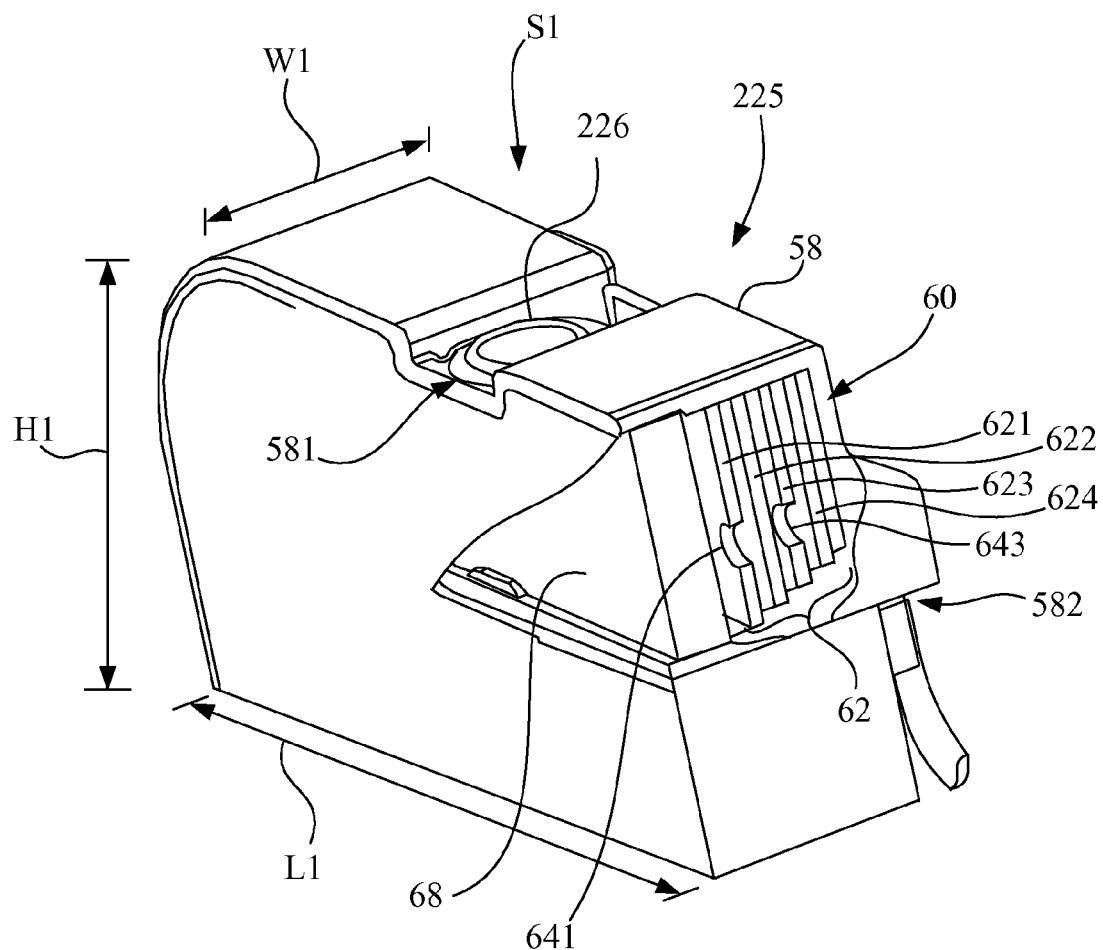
FIG. 5A is a perspective view of the fluid management tank of the disposable biopsy probe shown in FIGS. 2 and 3, with a portion broken away to expose a filter arrangement.

Referring also to FIG. 5A, fluid management tank 225 is fluidically interposed in the second vacuum path 22 between the first end 221 and the second end 222. Fluid management tank 225 includes a body 58 and a filter arrangement 60 contained within body 58 configured to prevent a flow of residual biopsy biological material, e.g., blood and particulate matter, from sample notch 444 of sample basket 441 to vacuum source 18 of driver assembly 12.

Body 58 of fluid management tank 225 has a first port 581 and a second port 582, with the second vacuum path 22 continuing between the first port 581 and the second port 582. The second port 582 of fluid management tank 225 is coupled to sample basket 441. Each of the second one-way valve 224 and the second vacuum seal element 226 of the second vacuum path 22 is coupled to the first port 581 of fluid management tank 225, and in the present embodiment, is mounted to an external surface of body 58 of fluid management tank 225.

Figure 5B:
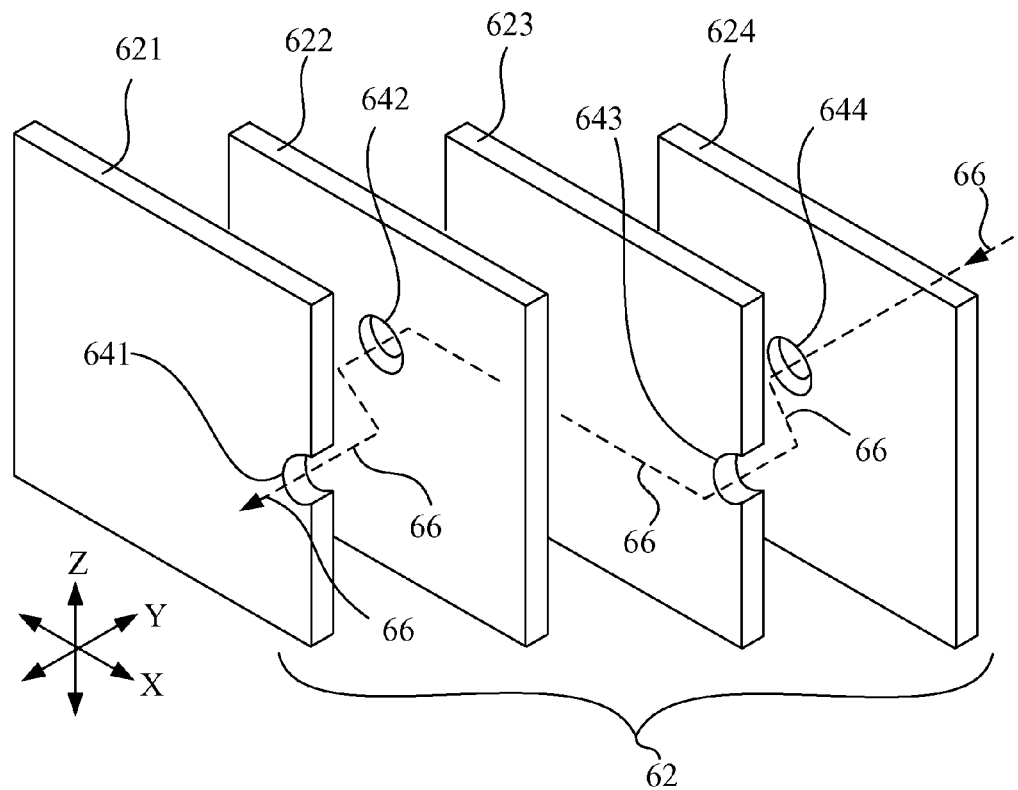
FIG. 5B is an exploded view of a plurality of fluid absorption layers of the filter arrangement of FIG. 5A.

As illustrated in FIGS. 5A and 5B, filter arrangement 60 includes a plurality of fluid absorption layers 62, individually identified as layers 621, 622, 623 and 624, arranged side by side, with each fluid absorption layer 621, 622, 623 and 624 being spaced apart from an adjacent fluid absorption layer e.g., 621 to 622, 622 to 623, 623, to 624. Each fluid absorption layer 621, 622, 623 and 624 has a respective through opening 641, 642, 643, 644, wherein adjacent through openings of through openings 641, 642, 643, 644 of the plurality of fluid absorption layers 62 are offset one to the next, e.g., in at least one of an X, Y, and Z direction, to form a tortuous open fluid passageway 66 through the plurality of fluid absorption layers 62. Each fluid absorption layer 621, 622, 623 and 624 may be, for example, a blotting paper.

Figure 5C:
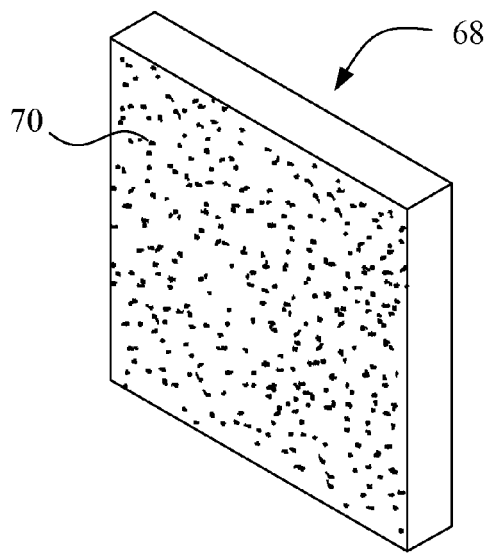
FIG. 5C is a perspective view of a porous filter element of the filter arrangement of FIG. 5A.

As illustrated in FIGS. 5A and 5C, filter arrangement 60 may further include a porous filter element 68 arranged to be fluidically in series with the plurality of fluid absorption layers 62 along the second vacuum path 22 that defines second passageway 227. The porous filter element 68 exhibits increased restriction to fluid flow as an increased number of pores 70 in the porous filter element 68 become clogged by residual biopsy biological material, such as blood and tissue particles. When a volume of the fluid flow through fluid management tank 225 has been reduced to a predetermined level, vacuum monitoring mechanism 30 senses the vacuum restriction, and controller 26 responds to shut off vacuum source 18.

Referring to FIGS. 6-13, each harvested tissue sample is transported out of the body of the patient and is collected by tissue sample retrieval mechanism 56. In general, tissue sample retrieval mechanism 56 collects tissue samples that have been harvested by scooping the tissue sample out of sample notch 444 of sample basket 441 of biopsy probe 44.

Figure 6:
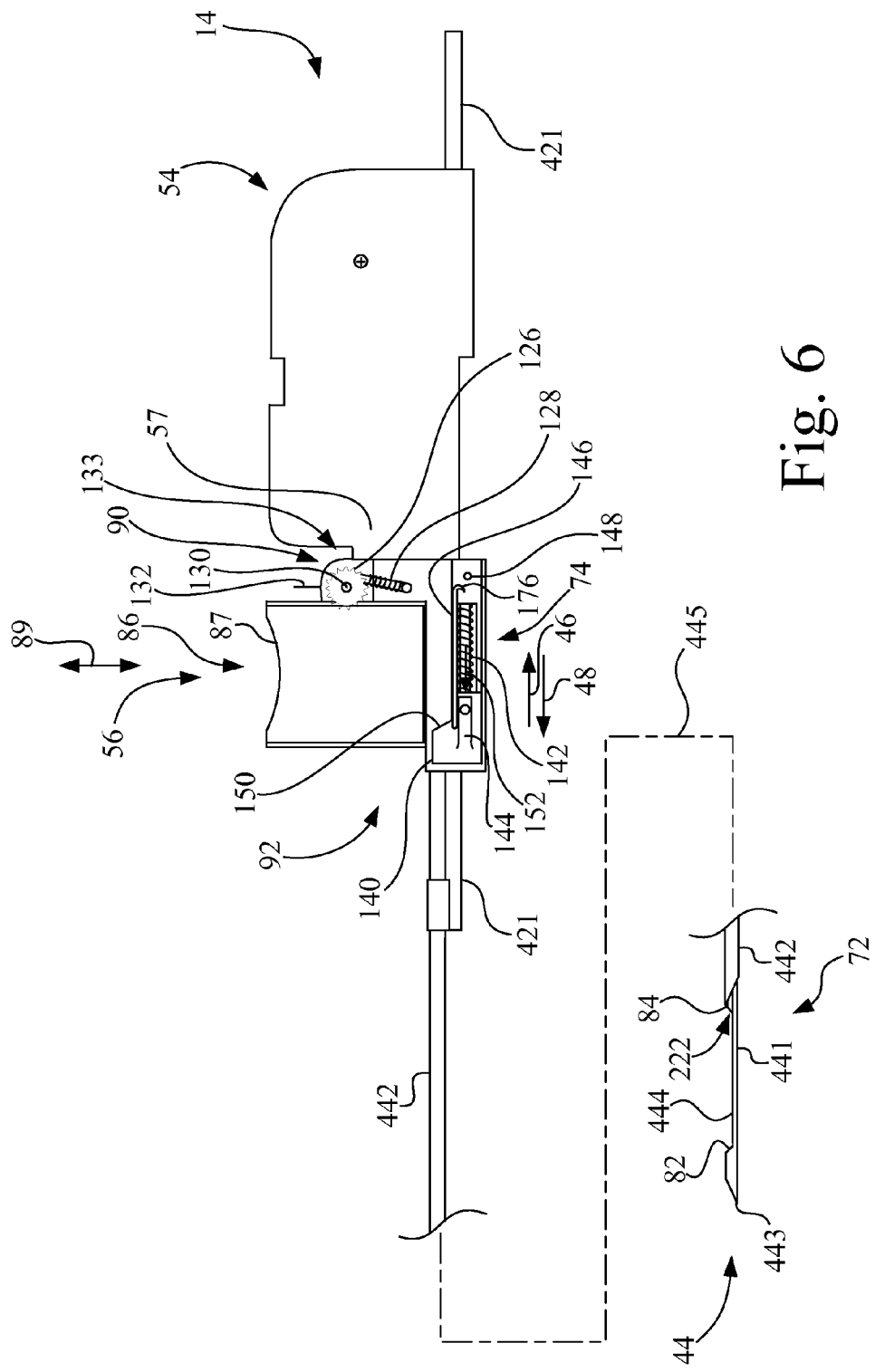
FIG. 6 is a side view of the disposable biopsy probe of FIG. 2 showing in further detail a tissue sample retrieval mechanism with the sample collection tank removed.
Figure 7:
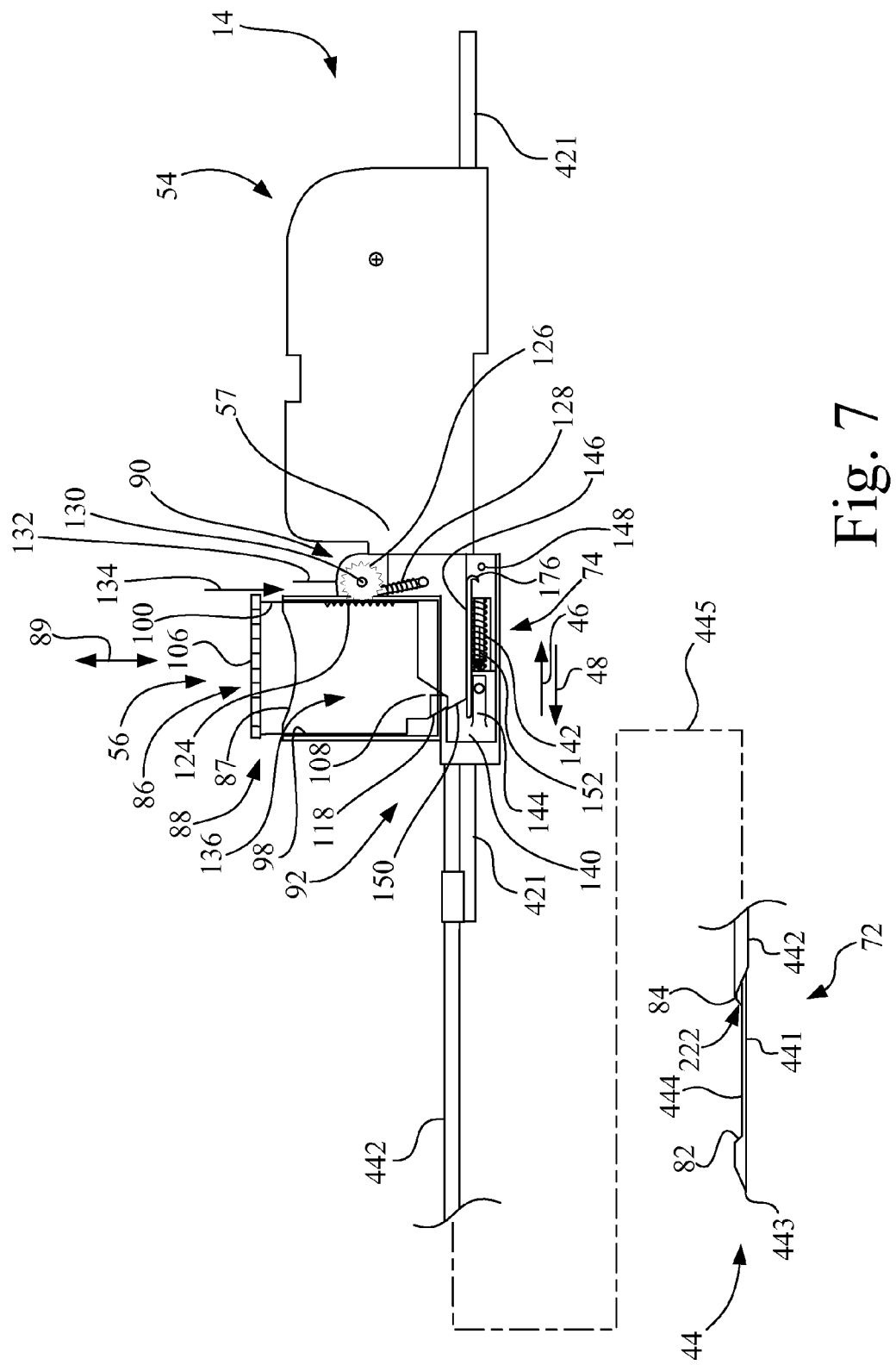
FIG. 7 is a side view of the disposable biopsy probe of FIG. 6 showing the tissue sample retrieval mechanism with the sample collection tank installed, and with the sample collection tank in the raised position.
Figure 8:
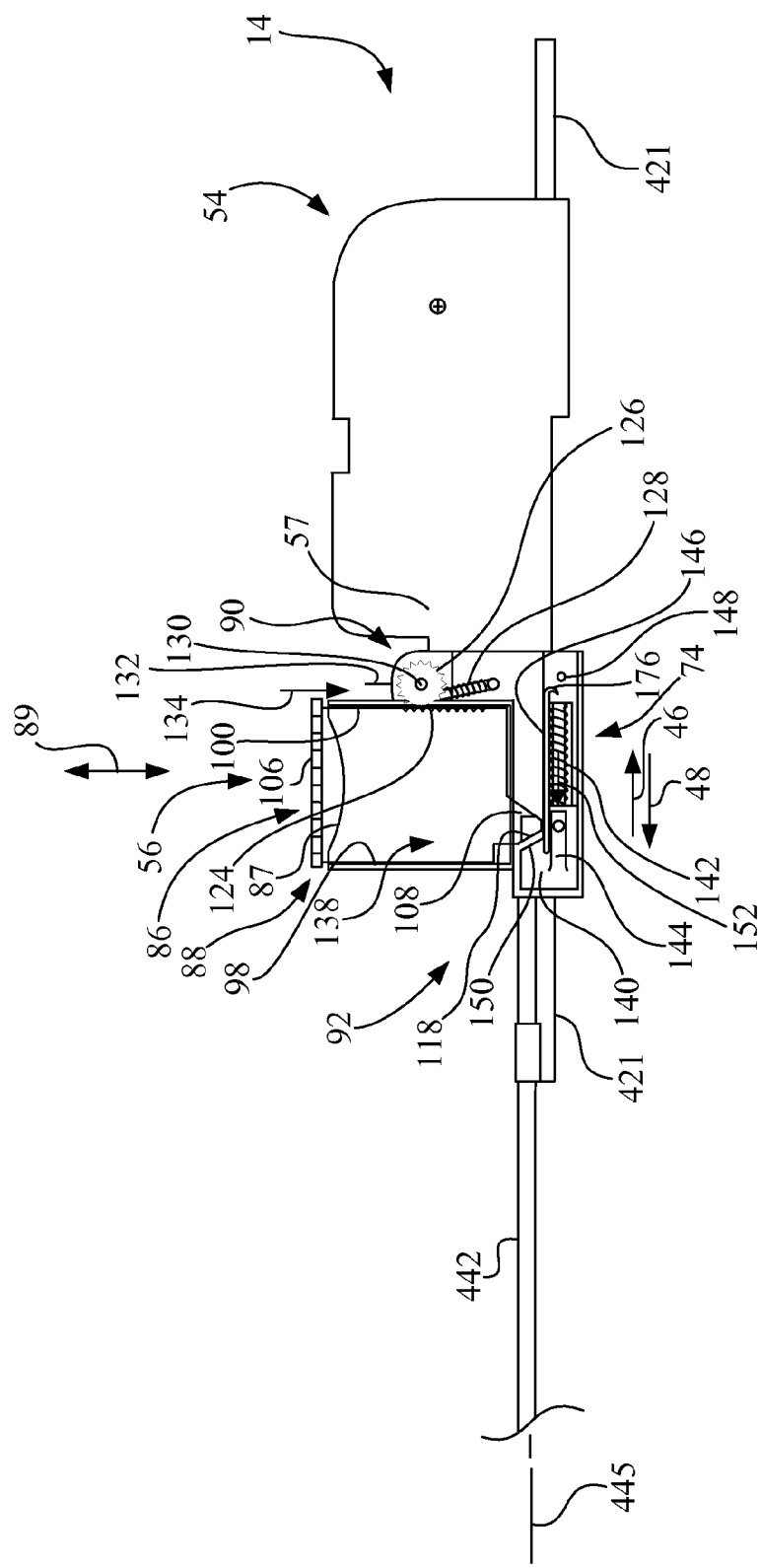
FIG. 8 is a side view of the disposable biopsy probe of FIG. 6 showing the tissue sample retrieval mechanism with the sample collection tank installed, and with the sample collection tank in the lowered collection position.
Figure 12:
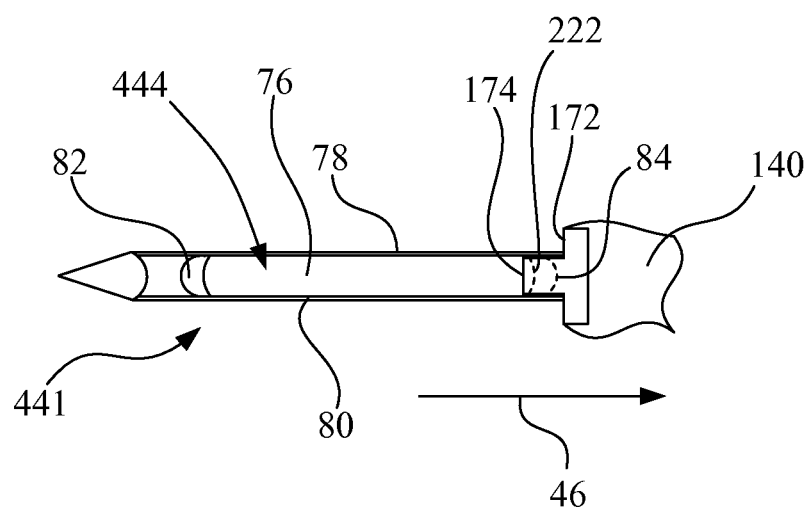
FIG. 12 is a top view of the sample basket and the lift member of the disposable biopsy probe of FIG. 7, with a portion of lift member broken away to expose a T-shaped stop, and a leaf spring tongue forming a portion of the T-shaped stop for removing residual tissue material and debris from a vacuum path at the sample notch of the sample basket.

Referring to FIGS. 6-9, biopsy probe 44 of biopsy probe assembly 14 includes a biopsy cannula, e.g., cutter cannula 442, and sample basket 441 arranged coaxially about longitudinal axis 445. Sample basket 441 having sample notch 444 is movably disposed relative to biopsy (cutter) cannula 442 along longitudinal axis 445 from a tissue harvesting position 72, as shown in FIGS. 6 and 7, to a tissue sample retrieval region 74, as illustrated in FIGS. 6-8 by electromechanical power source 28 and second drive 362, as more fully described above with respect to FIG. 3. Referring also to FIGS. 10 and 12, sample notch 444 is an elongate recessed region of sample basket 441 having a generally semicircular cross-section, and has a recessed floor 76, a pair of spaced elongate edges 78, 80 on opposite sides of recessed floor 76, a leading transition bevel 82, and a trailing transition bevel 84. Leading transition bevel 82 and trailing transition bevel 84 are located at opposite ends of the elongate recessed region, i.e., sample notch, 444.

In the present embodiment, tissue sample retrieval mechanism 56 includes a sample tank receptacle 86, a sample collection tank 88, a toggle mechanism 90, and a tank positioning mechanism 92. Sample collection tank 88 is configured for removable insertion into sample tank receptacle 86.

Sample tank receptacle 86, which may be formed integral with housing 57, includes a hollow guide 87 size to slidably receive sample collection tank 88. Thus, the configuration of sample tank receptacle 86 is such that sample tank receptacle 86 permits bi-directional movement of sample collection tank 88 in directions 89 (signified by double headed arrow) that are substantially perpendicular to longitudinal axis 445. Also, the configuration of sample tank receptacle 86 is such that sample tank receptacle 86 prohibits movement of sample collection tank 88 in a direction 46 or 48 along longitudinal axis 445.

Sample collection tank 88 defines a single collection cavity 94 (see FIG. 9) configured for receiving multiple tissue samples, such as tissue sample TS. Sample collection tank 88 has, in forming collection cavity 94, a base 96, a front wall 98, a rear wall 100, a pair of side walls 102, 104, and a removable cap 106. Sample collection tank 88 further includes a tissue sample scoop 108. Sample collection tank 88 is configured to collect a tissue sample directly from sample notch 444 as sample basket 441 moves along longitudinal axis 445 at tissue sample retrieval region 74. In this regard, tissue sample scoop 108 of sample collection tank 88 is configured to engage sample notch 444 of sample basket 441.

Tissue sample scoop 108 is fixed to and projects downwardly from base 96. Tissue sample scoop 108 extends forward toward a front portion 110 of sample collection tank 88 to terminate at a rim 112. Tissue sample scoop 108 has a tissue collection lumen 114 through which each tissue sample TS harvested by biopsy probe assembly 14 will pass. Tissue collection lumen 114 begins at an opening 116 located near rim 112 and extends to collection cavity 94. Tissue sample scoop 108 has a ramped face 118 located adjacent rim 112. Also, tissue sample scoop 108 has a first shoulder 120 and a second shoulder 122 that are positioned on opposite sides of opening 116.

A rack gear 124 is longitudinally (e.g., vertically) positioned on rear wall 100 of sample collection tank 88 to engage toggle mechanism 90.

Referring to FIGS. 6-9, toggle mechanism 90 is configured to aid in the mounting of sample collection tank 88 in sample tank receptacle 86, and to aid in the removal of sample collection tank 88 from sample tank receptacle 86. Toggle mechanism 90 is mounted to housing 57 and includes a rotary gear 126 and a spring 128. Rotary gear 126 has a rotational axis 130, e.g., an axle, which is attached to, or formed integral with, housing 57. Spring 128 is coupled between rotary gear 126 and housing 57, and is eccentrically mounted to rotary gear 126, i.e., at a location offset from rotational axis 130. Rotary gear 126 is located for driving engagement with rack gear 124 of sample collection tank 88, as sample collection tank 88 is slidably received by sample tank receptacle 86.

Referring to FIGS. 6-8, toggle mechanism 90 is configured to define a break-over point 132, e.g., at the 12:00 o'clock position in the orientation as shown. FIG. 6 shows an orientation of toggle mechanism 90 when sample collection tank 88 is not installed in hollow guide 87 of sample tank receptacle 86, where spring 128 is positioned beyond the 12 o'clock position in a clockwise direction in the orientation as shown, thus defining a home position 133 for toggle mechanism 90.

FIG. 7 shows an orientation of toggle mechanism 90 when sample collection tank 88 is installed (inserted) in hollow guide 87 of sample tank receptacle 86. As sample collection tank 88 is inserted in hollow guide 87 of sample tank receptacle 86, rack gear 124 of sample collection tank 88 engages rotary gear 126 and rotates rotary gear 126 about rotational axis 130 in the counterclockwise direction in the orientation as shown. When spring 128 is moved beyond break-over point 132, e.g., the 12 o'clock position, in the counterclockwise direction as sample collection tank 88 is slidably received by sample tank receptacle 86, spring 128 provides a biasing force 134, e.g., a downward pressure, via rotary gear 126 to bias sample collection tank 88 downwardly toward longitudinal axis 445. Thus, biasing force 134 exerts downward pressure on sample collection tank 88 when spring 128 is moved beyond the 12 o'clock position in the counterclockwise direction, in the orientation as shown in FIG. 7, and biasing force 134 is maintained when sample collection tank 88 is installed in sample tank receptacle 86.

Figure 9:
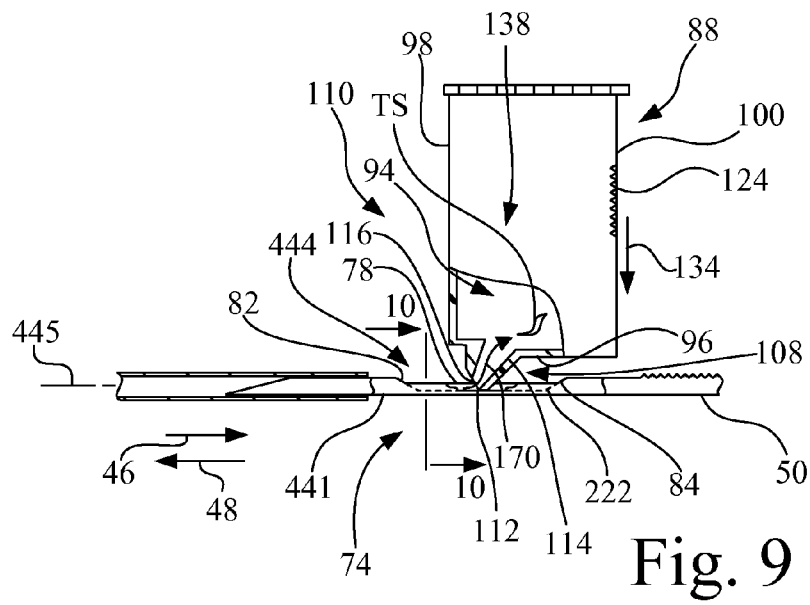
FIG. 9 is a side view of a portion of the tissue sample retrieval mechanism of FIG. 8 with a portion of the cutter cannula sectioned away to expose the retracting sample basket, and with a portion of the sample basket broken way to show the interaction of the tissue sample scoop of the sample collection tank with the sample notch.
Figure 11:
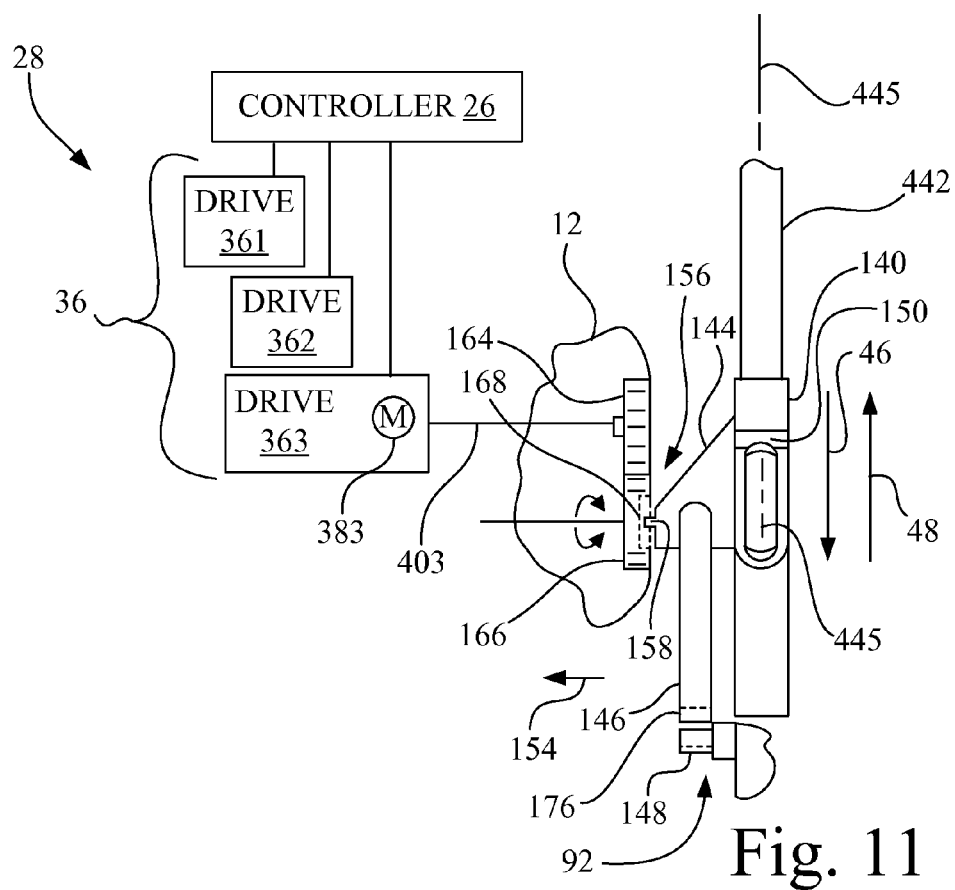
FIG. 11 is a top view of the tank positioning mechanism of FIG. 8.
Figure 10:
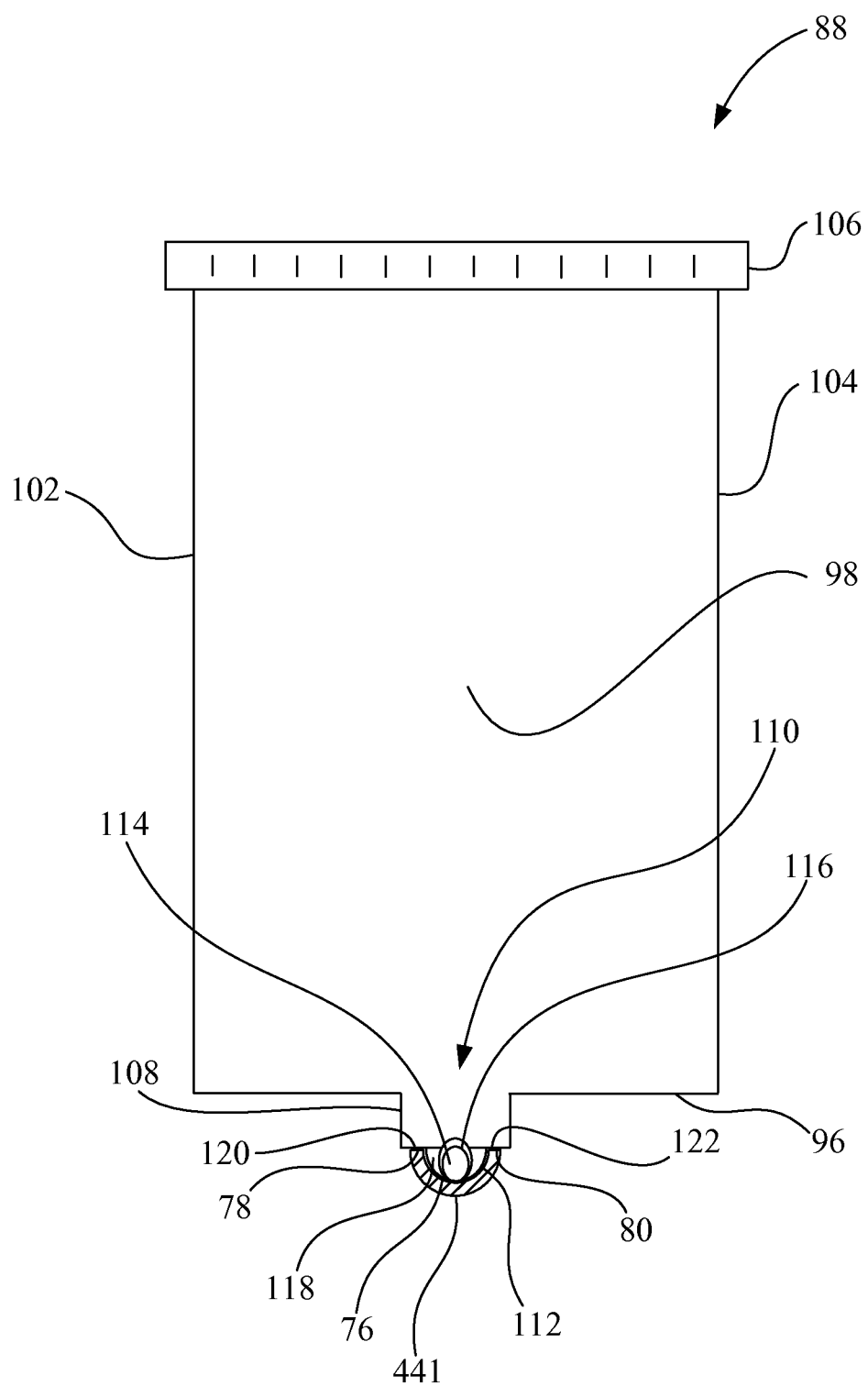
FIG. 10 is an enlarged front view of the sample collection tank of FIG. 9 showing the interaction of the rim of the sample collection tank with the sample basket shown in section along line 10-10 of FIG. 9.

Referring to FIG. 11 in conjunction with FIGS. 7-9, tank positioning mechanism 92 is configured to selectively move sample collection tank 88 between a raised position 136 illustrated in FIG. 7 and a lowered position 138 illustrated in FIGS. 8 and 9.

Tank positioning mechanism 92 is drivably engaged with electromechanical power source 28 to selectively lower, in conjunction with toggle mechanism 90, sample collection tank 88 from raised position 136 to lowered position 138 to position a portion, i.e., tissue sample scoop 108, of sample collection tank 88 in sliding engagement with sample notch 444 to facilitate collection of a tissue sample, e.g., tissue sample TS, from sample basket 441 as sample basket 441 is moved in tissue sample retrieval region 74. Also, electromechanical power source 28 is drivably engaged with tank positioning mechanism 92 and/or flexible toothed rack 50 to selectively raise sample collection tank 88, against the biasing force 134 exerted by toggle mechanism 90 and the biasing force 152 exerted by tank positioning mechanism 92, from lowered position 138 to raised position 136 to disengage sample collection tank 88 from sample notch 444 of sample basket 441 prior to, and following, tissue collection from sample basket 441.

More particularly, referring to FIGS. 6-8 and 11, tank positioning mechanism 92 includes a lift member 140, a spring 142, a lever 144, a latch member 146 and a latch catch 148.

Referring to FIGS. 7 and 8, lift member 140 is positioned along longitudinal axis 445. Lift member 140 has a ramp surface 150 positioned to engage ramped face 118 of sample collection tank 88. Spring 142 is positioned between lift member 140 and housing 57 to exert biasing force 152 on lift member 140 to bias ramp surface 150 in a direction away from ramped face 118 of sample collection tank 88.

As shown in FIG. 11, lever 144 extends from lift member 140 in a direction 154 perpendicular to longitudinal axis 445. Lever 144 has a distal end 156 configured to engage electromechanical power source 28, which may be in the form of a pin 158.

Electromechanical power source 28 is operable to move lift member 140 along longitudinal axis 445 in direction 46 to lift sample collection tank 88 away from longitudinal axis 445 as ramp surface 150 of lift member 140 slides along ramped face 118 of sample collection tank 88 Likewise, electromechanical power source 28 is operable to move lift member 140 along longitudinal axis 445 in direction 48 opposite direction 46 to lower sample collection tank 88 toward longitudinal axis 445 as ramp surface 150 of lift member 140 slides along ramped face 118 of sample collection tank 88.

As shown in FIG. 11, electromechanical power source 28 includes a lift drive 363 having an electrical motor 383 coupled to a motion transfer unit 403 (shown schematically in part by a line) that generally terminates at gears 164 and 166. Gear 166 includes a slot 168 for engaging pin 158 of lever 144. Motion transfer unit 403 provides rotary motion to gear 164, which in turn imparts rotary motion to gear 166. Motion transfer unit 403 may include one or more of a gear, gear train, belt/pulley arrangement, etc., for effecting at least a partial rotation of gear 164. Gear 166, however, is only rotated at a partial revolution, so as to effect a linear translation of pin 158 of lever 144, and in turn a linear translation of lift member 140.

The lowering of sample collection tank 88 for tissue sample collection (retrieval) is initiated by electromechanical power source 28 wherein gear 166 of lift drive 363 of electromechanical power source 28 is rotated in a direction to translate the lever 144, and in turn lift member 140, in direction 48 to lower sample collection tank 88. Biasing force 152 exerted on lift member 140 aids in moving ramp surface 150 in direction 48 away from ramped face 118 of sample collection tank 88. At this time, first shoulder 120 and second shoulder 122 of tissue sample scoop 108 are positioned for respective sliding engagement with the pair of spaced elongate edges 78, 80 of the elongate recessed region of sample notch 444 of sample basket 441 along longitudinal axis 445.

More particularly, with reference to FIGS. 8 and 11, the translation of the lever 144 and in turn lift member 140 in direction 48 causes the oblique face ramped face 118 of sample collection tank 88 to slide down the oblique ramp surface 150 of lift member 140, and tissue sample scoop 108 with rim 112 are moved into the elongate recessed region of sample notch 444 of sample basket 441 toward recessed floor 76. Referring also to FIGS. 9 and 10, continued transport of the sample notch 444 in direction 46 by electromechanical power source 28 will cause rim 112 of tissue sample scoop 108 to slide along recessed floor 76 and along the sides between elongate edges 78, 80 of sample notch 444, scooping up the tissue sample TS and transporting the tissue sample TS through tissue collection lumen 114 into collection cavity 94 of sample collection tank 88 along path 170. The shoulders 120, 122 of sample collection tank 88 are configured to slide along the upper spaced elongate edges 78, 80 of sample basket 441, ensuring that no tissue sample material is pushed out of sample notch 444.

The raising of sample collection tank 88 occurs near the conclusion of the tissue collection sequence. Near the conclusion of the tissue collection sequence, the further movement of sample notch 444 of sample basket 441 in direction 46 by operation of electromechanical power source 28 and second drive 362 is transferred to lift member 140 by a driving engagement of sample basket 441 in direction 46 with a T-shaped stop 172 (see FIG. 12) attached to lift member 140, causing lift member 140 to move in direction 46. The scoop rim 112 of sample collection tank 88 reaches the sloping leading transition bevel 82 of sample notch 444 and is pushed upwards by the interplay between ramped face 118 of sample collection tank 88 and leading transition bevel 82 of sample notch 444, thus beginning to raise sample collection tank 88. As lift member 140 is further moved in direction 46 by movement of sample notch 444, the scoop rim 112 leaves sample notch 444 and ramped face 118 of sample collection tank 88 and comes to rest against ramp surface 150 of lift member 140, which closes off tissue collection lumen 114 of sample collection tank 88 and prevents the tissue sample TS from falling out of tissue collection lumen 114.

In addition, lift drive 363 is rotated to ensure that lift member 140 is translated fully in direction 46 in the event that the force exerted by sample notch 444 is insufficient to accomplish the translation. More particularly, electromechanical power source 28 rotates gear 166 of lift drive 363 in a direction to translate the lever 144 in direction 46. Thus, electromechanical power source 28 facilitates movement of lift member 140 along longitudinal axis 445 in first direction 46 against the biasing force 152 exerted by spring 142 to lift sample collection tank 88 as ramp surface 150 of lift member 140 slides along ramped face 118 of sample collection tank 88.

At the conclusion of the transport of sample notch 444 in direction 46 towards the proximal end of driver assembly 12, a leaf spring tongue 174 of T-shaped stop 172 (see FIG. 12) removes residual tissue material and debris from the second end 222 of vacuum path 22 at trailing transition bevel 84 of sample notch 444 to ensure that a sufficient vacuum may be drawn into sample notch 444.

Referring again to FIGS. 6-8, 11 and 13, latch member 146 is attached to, or formed integral with, lift member 140. Latch member 146 extends from lever 144 in direction 46, and has a distal hook 176. Latch member 146 is located for engagement with latch catch 148 to latch lift member 140 in a transport latched position, shown in FIG. 13, corresponding to raised position 136 of sample collection tank 88. Latch catch 148 may be attached to, or formed integral with, housing 57.

Figure 13:
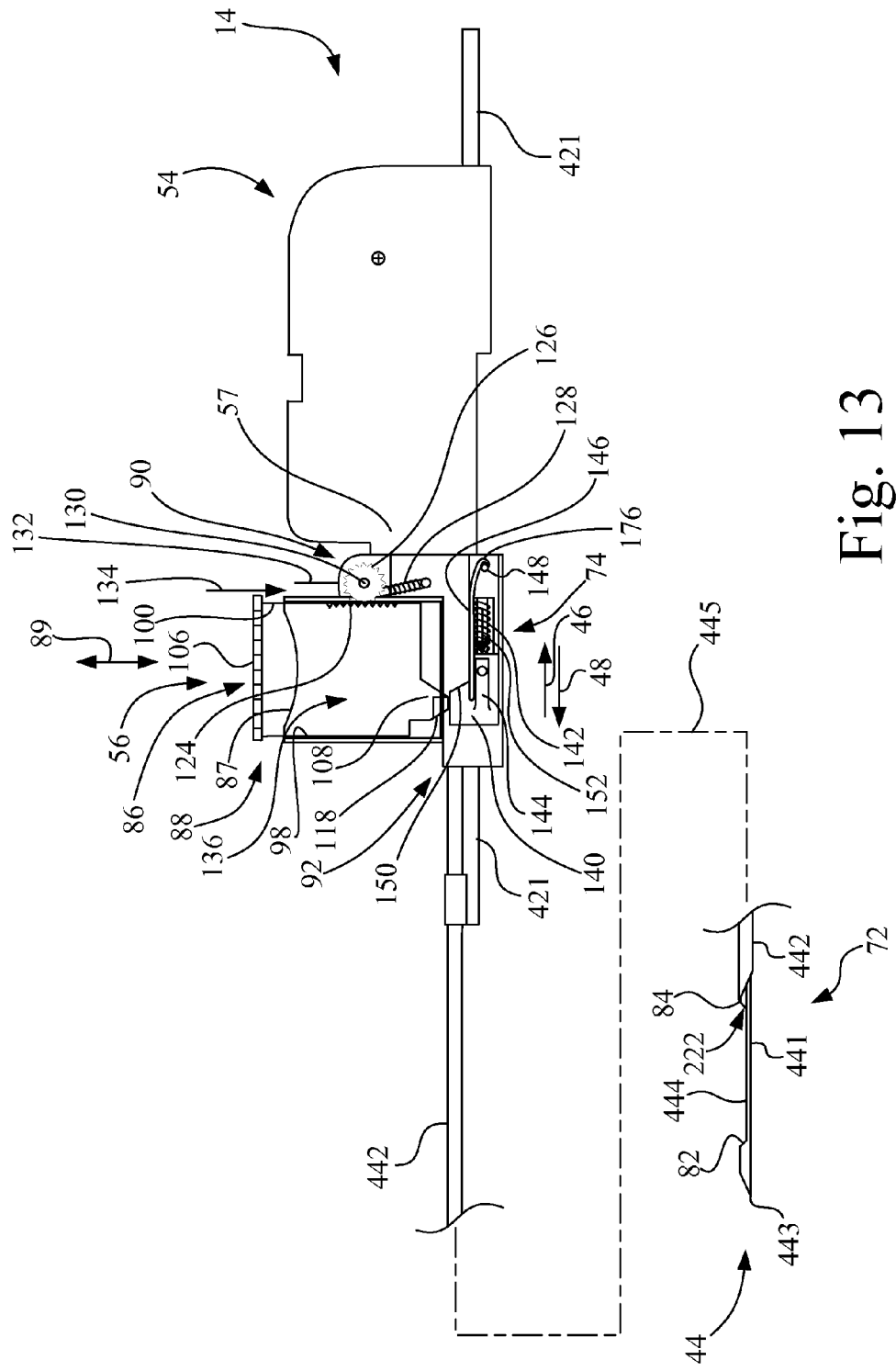
FIG. 13 is a side view of the disposable biopsy probe of FIG. 7 showing the latch member of the tank positioning mechanism in the latched transport position.

One purpose of latch member 146 is to maintain the proper insertion position of lever 144 during transport of biopsy probe assembly 14 to ensure proper insertion of biopsy probe assembly 14 in driver assembly 12. Prior to insertion of biopsy probe assembly 14 in driver assembly 12, lever 144 is held in a latched transport position, which is the only position permitting pin 158 at distal end 156 of lever 144 to be inserted into slot 168 (e.g., a driver recess) of lift drive 363 (see FIG. 11). In the latched transport position, as illustrated in FIG. 13, the lever 144 is held in position by latch member 146 that is held in tension against latch catch 148 by pressure (biasing force 152) from spring 142. Thus, insertion of biopsy probe assembly 14 in driver assembly 12 in the latched transport position results in placement of pin 158 at distal end 156 of lever 144 in slot 168 (e.g., a driver recess) of lift drive 363.

A second purpose of the latch member 146 is to prevent accidental reuse of the disposable probe. As part of power up, the lift drive 363 engages pin 158 at distal end 156 of lever 144 and moves lever 144 in direction 46 to a fully retracted position, which in turn causes latch member 146 to move out of engagement with latch catch 148. The tension of the latch member 146 is released, causing latch member 146 to move out of the plane of latch catch 148 and preventing latch member 146 from reestablishing contact with latch catch 148. Since spring 142 will bias lift member 140 in direction 48, the latched transport position illustrated in FIG. 13 may not be reestablished once biopsy probe assembly 14 has been removed from driver assembly 12. Since the latched transport position is the only position permitting biopsy probe assembly 14 to be inserted in driver assembly 12, accidental reuse of biopsy probe assembly 14 is prevented.

Figure 14:
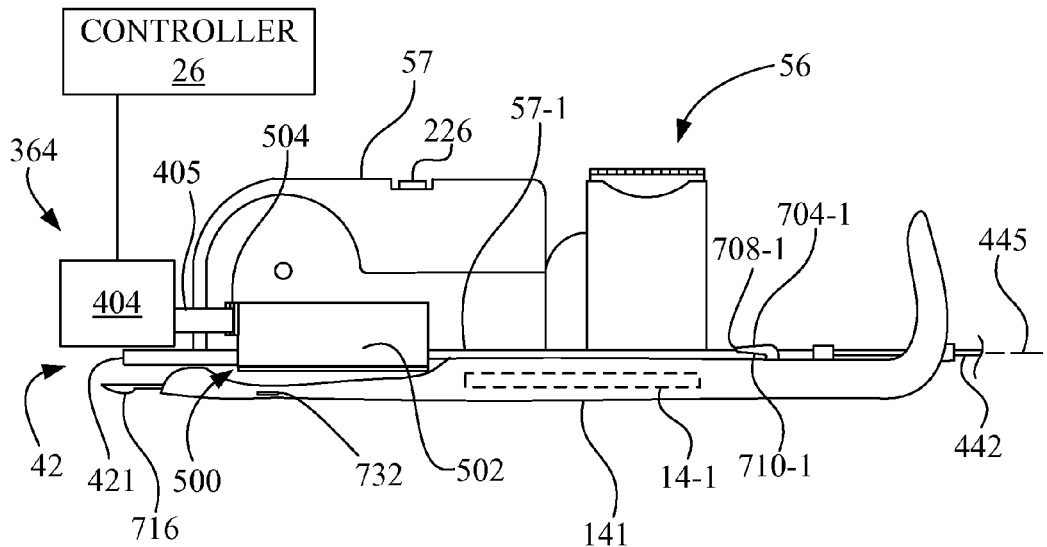
FIG. 14 is a side view of a portion of the biopsy probe assembly of FIG. 1, opposite to the side view shown in FIG. 2, and illustrating a slider assembly.

Referring now to FIG. 14, there is shown a side view of a portion of the biopsy probe assembly 14 of FIG. 1, opposite to the side view shown in FIG. 2. Biopsy probe assembly 14 further includes a slider assembly 500, which is drivably engaged with a slider drive 364 of biopsy probe assembly. Slider drive 364 is communicatively coupled to controller 26. Slider drive 364 and slider assembly 500 cooperate to provide a switching, for example, between a tissue harvesting mode and a piercing shot mode. In the tissue harvesting mode, cutter cannula 442 is able to move independent of sample basket 441, wherein first driven unit (cannula driver) 421 attached to cutter cannula 442 may be advanced relative to sample basket 441 to sever tissue present in sample basket 441. In the piercing shot mode, cutter cannula 442 and sample basket 441 move in unison, wherein stored energy, e.g., a compressed spring, in motion transfer unit 401 is transferred to first driven unit (cannula driver) 421 in an abrupt manner to fire cutter cannula 442 and sample basket 441 in unison to aid in inserting biopsy probe 44 into fibrous tissue.

Figure 15A:
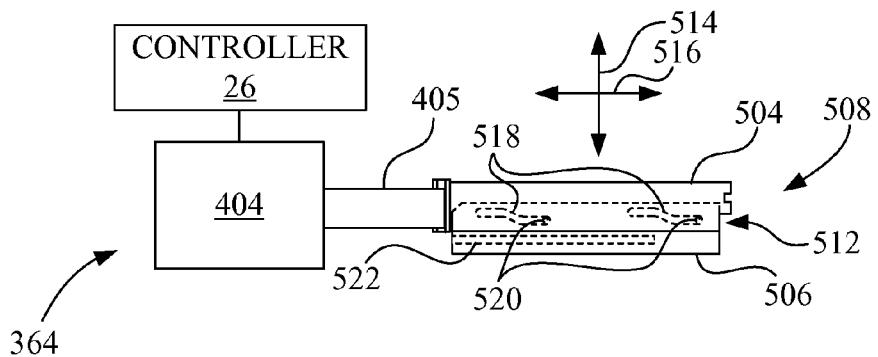
FIG. 15A shows the slider driver and slider of the slider assembly of FIG. 14, with the slider in the raised position.
Figure 15B:
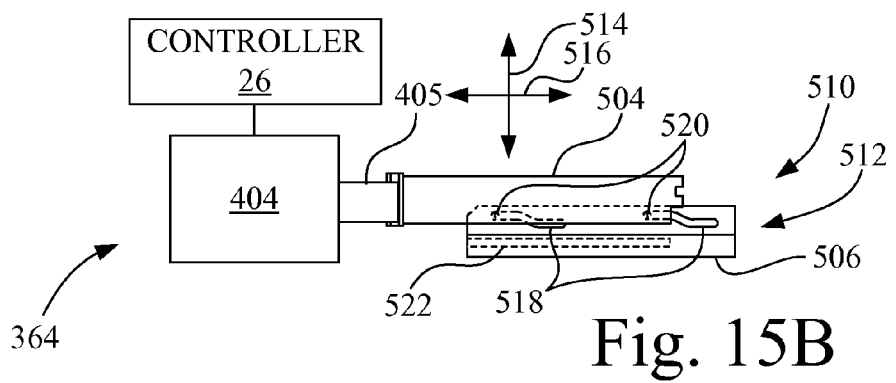
FIG. 15B shows the slider driver and slider of the slider assembly of FIG. 14, with the slider in the lowered position.

Slider drive 364 includes a motion transfer unit 404 that is configured to facilitate a linear movement of a coupling pawl 405 between an extended tissue harvesting position, as shown in FIG. 15A, and a retraced piercing shot position, as shown in FIG. 15B, in a direction parallel to longitudinal axis 445. Motion transfer unit 404 of slider drive 364 is configured with a linear motion converter, such as for example a worm gear arrangement, rack and pinion arrangement, etc., or a solenoid-slide arrangement, etc.

Slider assembly 500 includes a housing 502 (FIG. 14) that contains a slider driver 504 and slider 506 (FIGS. 15A, 15B). FIG. 15A shows the orientation of slider driver 504 and slider 506 when slider assembly 500 of biopsy probe assembly 14 is in the tissue harvesting position, with slider 506 in the vertically raised position 508. FIG. 15B shows the orientation of slider driver 504 and a slider 506 when slider assembly 500 of biopsy probe assembly 14 is in the piercing shot position, with the slider 506 in the vertically lowered position 510.

Slider driver 504 and slider 506 are coupled in a sliding relationship via a cam/cam follower arrangement 512 to facilitate the vertical translation of slider 506 between the vertically raised position 508 and the vertically lowered position 510. Housing 502 restrains slider driver 504 from lifting/lowering movement in directions 514, while facilitating motion in directions 516 substantially parallel to longitudinal axis 445 (see FIGS. 14-15B). Likewise, housing 502 restrains slider 506 from movement in directions 516, while facilitating lifting/lowering motion in directions 514.

In the exemplary embodiment shown in FIGS. 15A and 15B, a pair of cam channels 518 is formed in slider 506 which provide a ramp to facilitate the lifting and lowering of slider 506 in directions 514. A pair of cam follower pins 520 is formed on a side wall of slider driver 504 and located to correspondingly engage the pair of cam channels 518 of slider 506. Accordingly, in the orientation shown in FIG. 15A, movement of slider driver 504 to the right (coupling pawl 405 extended, slider driver 504 retracted) results in slider 506 being placed in the vertically raised position 508. Conversely, in the orientation shown in FIG. 15B, movement of slider driver 504 to the left (coupling pawl 405 retracted, slider driver 504 extended) results in slider 506 being placed in the vertically lowered position 510.

As shown in FIGS. 15A, 15B and 22F, slider 506 includes a slider groove 522. Slider groove 522 is formed in a side wall 758 of slider 506, and is arranged to be substantially horizontal.

Figure 16A:
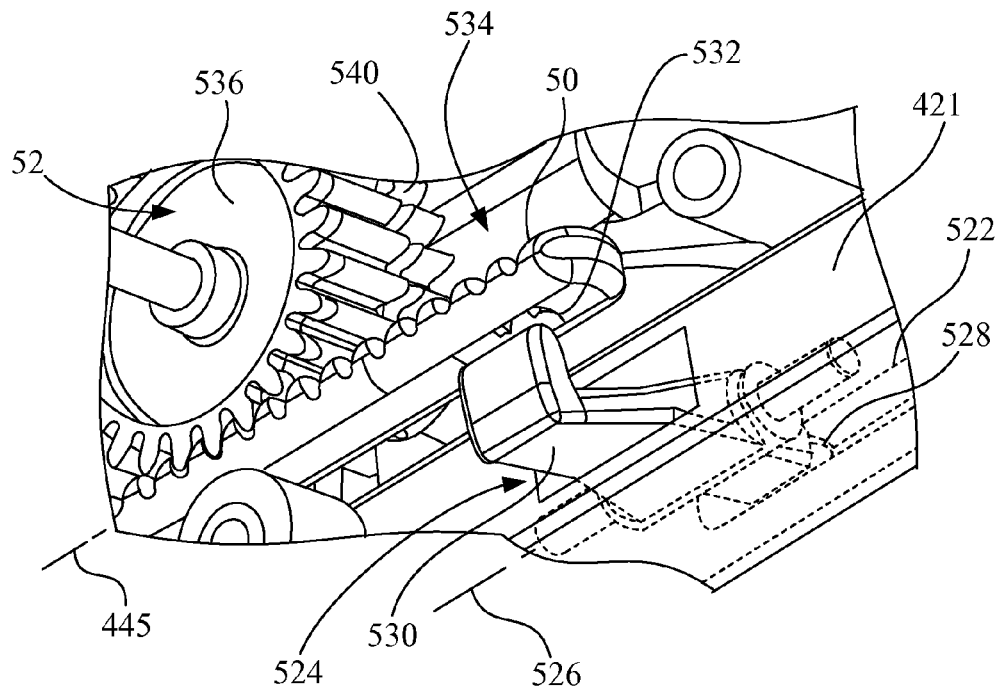
FIG. 16A is a perspective view showing the flexible tooth rack and a pivot member that selectively engages the flexible toothed rack, with the pivot member disengaged from the flexible toothed rack.

Referring to FIG. 16A, a pivot member 524 is pivotably coupled to first driven unit (cannula driver) 421 to pivot about a pivot axis 526, with pivot axis 526 being oriented substantially parallel to longitudinal axis 445 (see also FIG. 14). Pivot member 524 has a hook pin 528 located on one side of pivot axis 526, and has a rack hook 530 located on the other side of pivot axis 526. Hook pin 528 is drivably engaged by slider groove 522 of slider 506 of slider assembly 500.

Accordingly, when slider 506 is positioned in the raised position 508, thus raising hook pin 528, then rack hook 530 is lowered so that rack hook 530 is disengaged from connecting slot 532 formed in the proximal end 534 of flexible toothed rack 50, as shown in FIG. 16A, thus facilitating operation in the tissue harvesting mode. Conversely, when slider 506 is positioned in the lowered position 510, thus lowering hook pin 528, then rack hook 530 is raised so that rack hook 530 is engaged with connecting slot 532 formed in the proximal end 534 of flexible toothed rack 50, as shown in FIG. 16B, thus facilitating operation in the piercing shot mode.

Figure 17A:
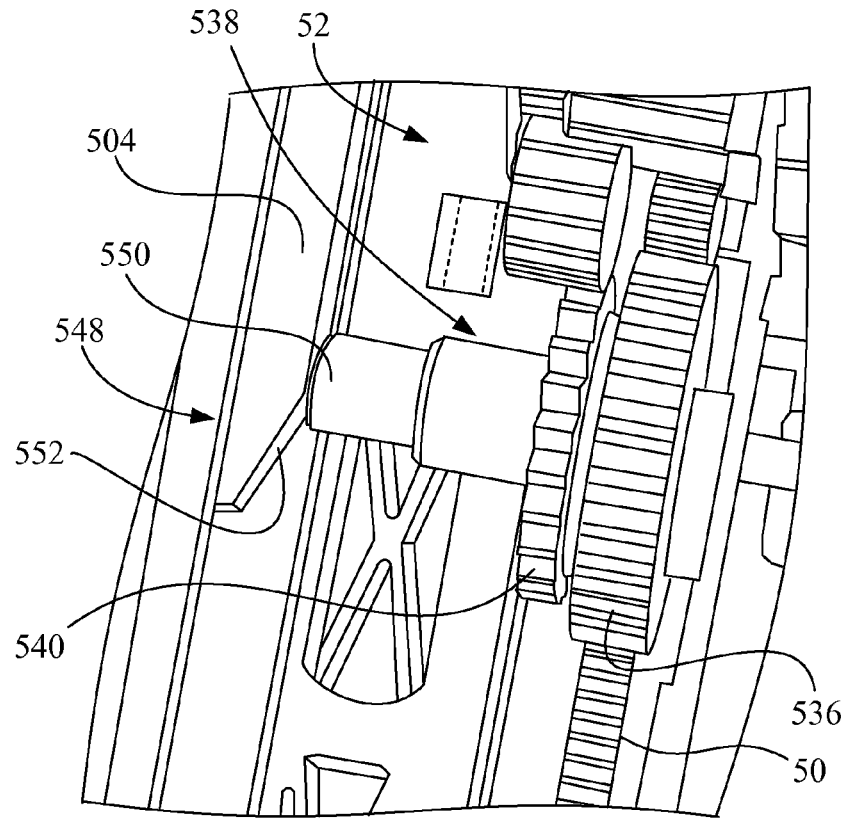
FIG. 17A is a perspective view of a clutch drive having an intermediate gear drivably engaged with a rack drive gear.

Referring now also to FIG. 17A, in conjunction with FIG. 16A, there is show a portion of gear train 52 that is drivably engaged with the teeth of flexible toothed rack 50 (FIG. 16A). More particularly, gear train 52 includes a rack drive gear 536 having teeth that drivably engage the teeth of flexible toothed rack 50. As previously described, a distal end of flexible toothed rack 50 is drivably connected to sample basket 441 (see FIG. 3). A clutch drive 538, including an intermediate gear 540, drivably engages rack drive gear 536.

Figure 16B:
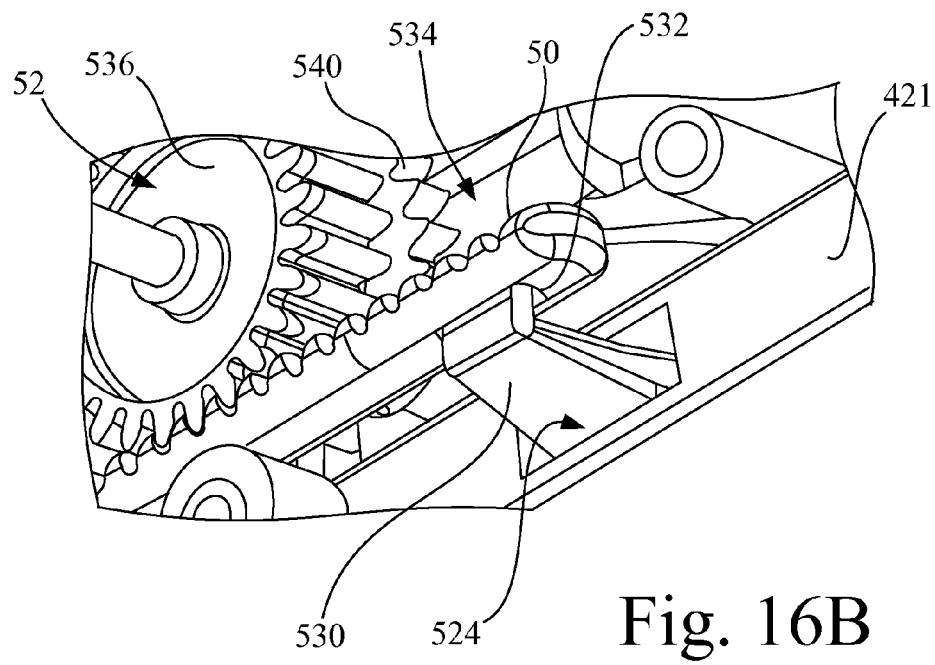
FIG. 16B is a perspective view showing the flexible tooth rack and a pivot member that selectively engages the flexible toothed rack, with the pivot member engaged with the flexible toothed rack.
Figure 17B:
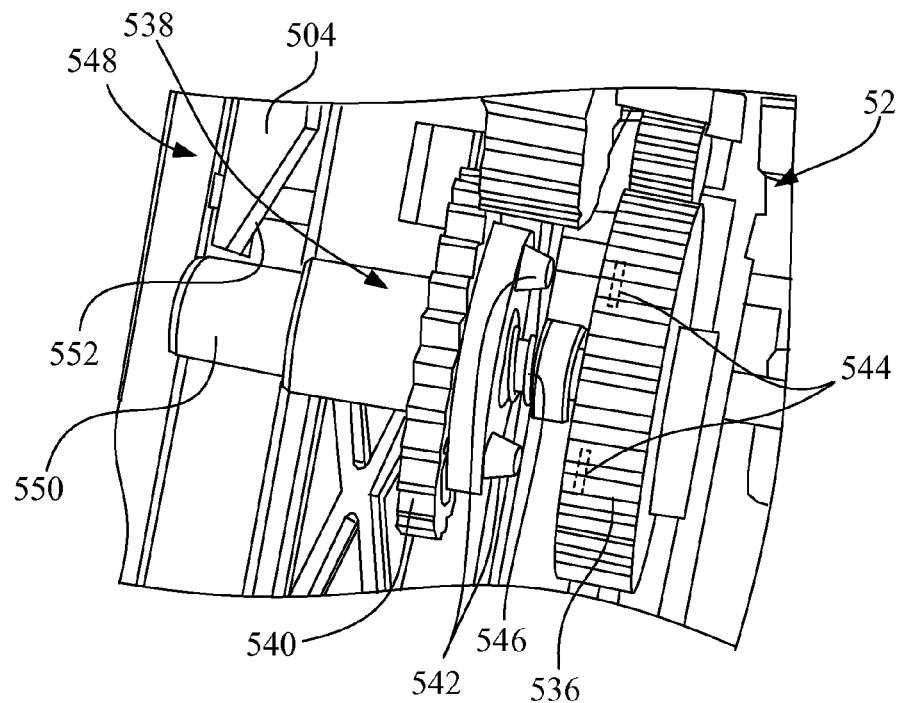
FIG. 17B is a perspective view of a clutch drive having the intermediate gear disengaged from driving the rack drive gear.

Referring now also to FIG. 17B, in conjunction with FIG. 16B, intermediate gear 540 includes driving pins 542 that drivably engage corresponding slots 544 in rack drive gear 536, such that when driving pins 542 are engaged with slots 544, a rotation of intermediate gear 540 results in a corresponding rotation of rack drive gear 536, resulting in a linear translation of flexible toothed rack 50. Also, as shown in FIG. 17B, clutch drive 538 includes a spring 546 that tends to bias intermediate gear 540 out of engagement with rack drive gear 536.

Referring again to FIGS. 15A and 17A, movement of slider driver 504 to the right (coupling pawl 405 extended and slider driver 504 retracted) results in a distal portion 548 of slider driver 504 being positioned to press on an axle extension 550 of intermediate gear 540, thus overcoming the biasing force of spring 546 (see FIG. 17B), and holding intermediate gear 540 in engagement with rack drive gear 536. To aid in the translation of intermediate gear 540 to compress spring 546 and to drivably engage rack drive gear 536, the distal portion 548 of slider driver 504 includes a beveled surface 552. As set forth above, the movement of slider driver 504 to the right (coupling pawl 405 extended and slider driver retracted) disengages rack hook 530 from flexible toothed rack 50 (see also FIG. 16A). Accordingly, biopsy probe assembly 14 is in the tissue harvesting mode, and gear train 52 of second driven unit 422 is enabled to drive flexible toothed rack 50 via rack drive gear 536.

Referring again to FIGS. 15B and 17B, movement of slider driver 504 to the left (coupling pawl 405 retracted and slider driver 504 extended) results in the distal portion 548 of slider driver 504 being positioned to release axle extension 550 of intermediate gear 540, thus permitting the biasing force of spring 546 to separate intermediate gear 540 from engaging rack drive gear 536. Thus, gear train 52 of second driven unit 422 is disengaged from driving flexible toothed rack 50. As set forth above, the movement of slider driver 504 to the left (coupling pawl 405 retracted and slider driver 504 extended) engages rack hook 530 with flexible toothed rack 50 (see FIG. 16B). Accordingly, biopsy probe assembly 14 is in the piercing shot mode, thereby permitting cutter cannula 442 and sample basket 441 to move in unison with the movement of first driven unit (cannula driver) 421 engaged with motion transfer unit 401 of first drive 361 of driver assembly 12.

Figure 18:
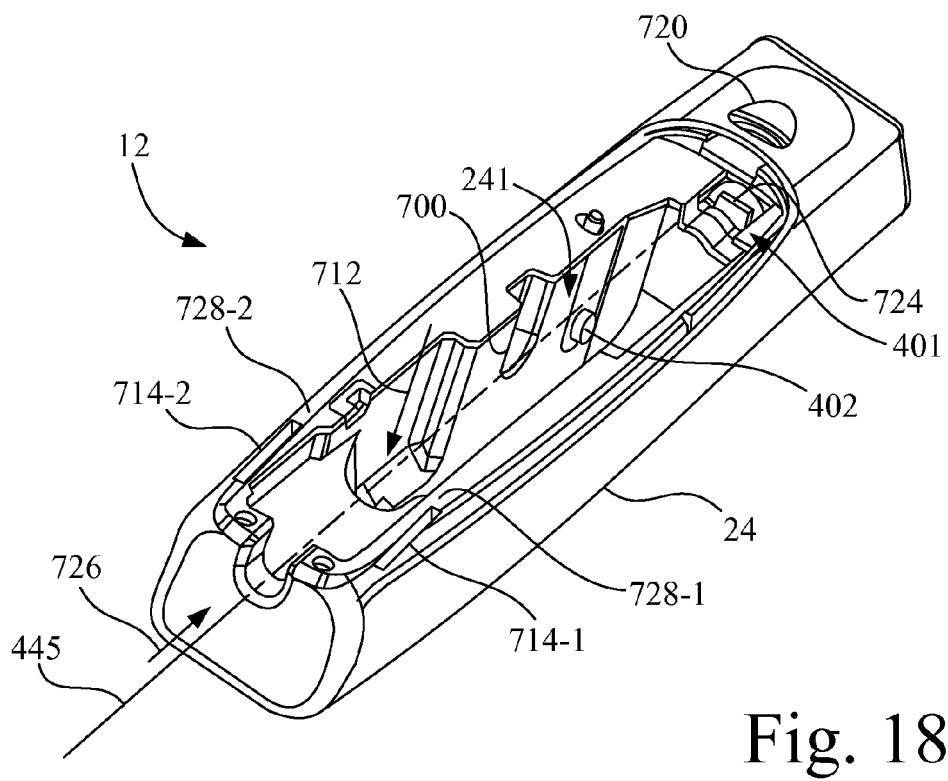
FIG. 18 is a bottom perspective view of the driver assembly of FIG. 1.
Figure 19:
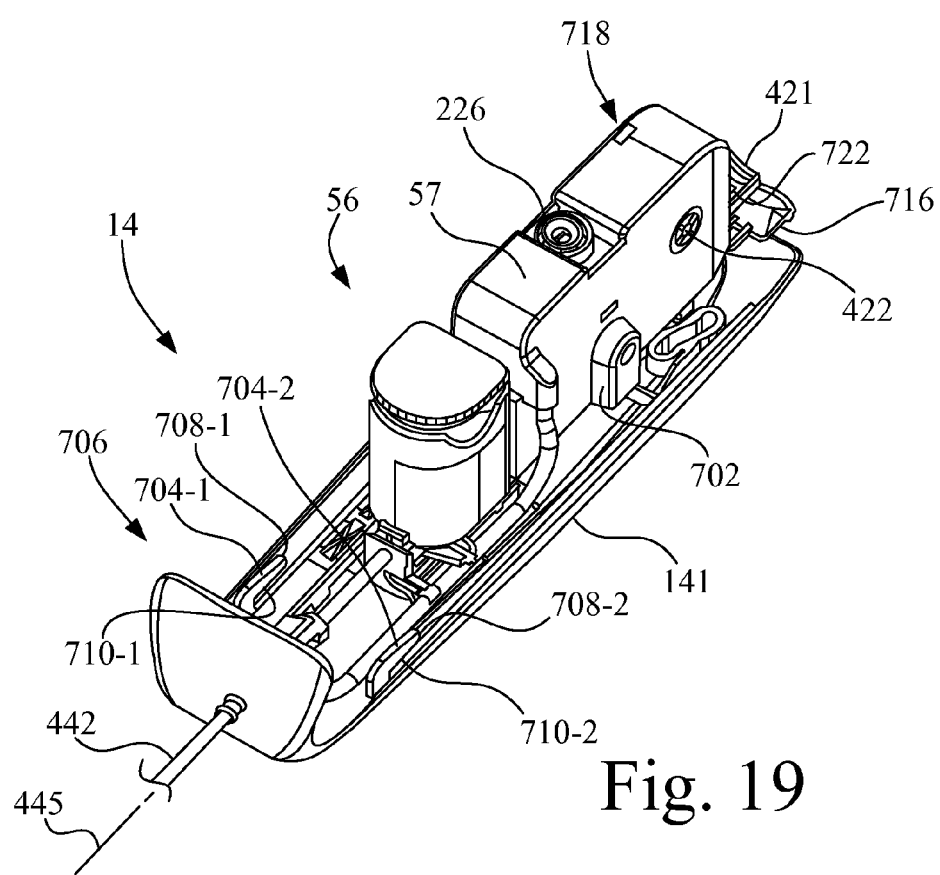
FIG. 19 is a perspective view of a portion the biopsy probe assembly of FIG. 1.

Referring now to FIGS. 18 and 19, the general sequence of mounting of a new biopsy probe assembly 14 to driver assembly 12 will be described.

Elongate cavity 241 of driver assembly 12 is shaped to snugly receive housing 57 of biopsy probe assembly 14. For example, a slot 700 defined in elongate cavity 241 corresponds in shape to a protrusion 702 of housing 57 (see FIG. 18) to resist longitudinal movement of housing 57 relative to driver assembly 12 along longitudinal axis 445 after housing 57 is seated in elongate cavity 241.

As shown in FIG. 19, biopsy probe assembly 14 includes a pair of rearwardly facing cantilever rails 704-1, 704-2 attached to a far end portion 706 of cover 141. Each of cantilever rails 704-1, 704-2 has a respective free end 708-1, 708-2 and a respective interior edge 710-1, 710-2 that is slightly inclined in a direction toward the free end respective free end 708-1, 708-2. Cantilever rails 704-1, 704-2 of biopsy probe assembly 14 are positioned to be received in a direction 712 substantially orthogonal to longitudinal axis 445 by corresponding locking slots 714-1, 714-2 formed in housing 24 of driver assembly 12. Biopsy probe assembly 14 includes a latch tab 716 attached to a near end 718 of cover 141 which is positioned to be received by the corresponding tab slot 720 in housing 24 of driver assembly 12.

Biopsy probe assembly 14 is mounted to driver assembly 12 as follows. Housing 57 of biopsy probe assembly 14 is seated in elongate cavity 241 of driver assembly 12. As housing 57 of biopsy probe assembly 14 is seated in elongate cavity 241 of driver assembly 12, first driven unit 421 (e.g., a linear cannula driver) of transmission device 42 of biopsy probe assembly 14 is drivably engaged by motion transfer unit 401 of first drive 361 of driver assembly 12 (see also FIG. 3). More particular, as shown in FIG. 19, first driven unit 421 (e.g., a linear cannula driver) of transmission device 42 of biopsy probe assembly 14 includes a driver slot 722 into which a metal tongue 724 of motion transfer unit 401 of first drive 361 of driver assembly 12 is drivably engaged. In addition, motion transfer unit 402 is engaged with second driven unit 422 (see FIGS. 18 and 19), and motion transfer unit 403 is engaged with tank positioning mechanism 92 (see FIG. 11). Also, coupling pawl 405 of motion transfer unit 404 is engaged with slider driver 504 of slider assembly 500, as shown in FIG. 14. Further, referring also to FIGS. 4A and 4B, as housing 57 of biopsy probe assembly 14 is seated in elongate cavity 241 of driver assembly 12, the first vacuum seal element 206 of the driver assembly 12 is brought into contact with the second vacuum seal element 226 of the disposable biopsy probe assembly 14.

To complete the mounting process, referring again to FIGS. 18 and 19, cover 141 of biopsy probe assembly then is slid relative to housing 57 in direction 726, which is substantially parallel to longitudinal axis 445, such that the inclined interior edge 710-1, 710-2 of rearwardly facing cantilever rails 704-1, 704-2 extend under corresponding portions 728-1, 728-2 of housing 24 proximal to locking slots 714-1, 714-2 in tightening engagement as cover 141 is slid in direction 726. Concurrently with the sliding of cover 141, latch tab 716 of biopsy probe assembly 14 is received in tab slot 720 in housing 24 of driver assembly 12 to releasably latch cover 141 in its foremost sliding position relative to driver assembly 12.

As may be recognized from the discussion above, due to mechanical complexities in the design of driver assembly 12 and biopsy probe assembly 14, to insure proper mounting of biopsy probe assembly 14 to driver assembly 12 the mechanical components of each of driver assembly 12 and biopsy probe assembly 14 must in the proper positions relative to each other prior to and during installation of biopsy probe assembly 14 in driver assembly 12.

For example, prior to installing biopsy probe assembly 14 in driver assembly 12, driver assembly 12 is to be in an initialized state, and if not already in the initialized state, then driver assembly 12 is placed in the initialized state. With reference also to FIGS. 3, 11, 14 and 18, the initialed state of driver assembly 12 is achieved when the mechanical components (e.g., motion transfer unit 401, motion transfer unit 402, motion transfer unit 403, and motion transfer unit 404, respectively) of drives 361, 362, 363, and 364 of electrical drive assembly 36 of electromechanical power source 28 of driver assembly 12 are prepositioned to correspond to the factory preset state of a new biopsy probe assembly 14, to thereby facilitate the proper mechanical drivable coupling between driver assembly 12 and biopsy probe assembly 14.

For example, if the mechanical components of drives 361, 362, 363, and 364 are not in the proper position to facilitate a coupling of driver assembly 12 to biopsy probe assembly 14, an error state exists and driver assembly 12 will need to be reset to the initialized state. The reset sequence of driver assembly 12 may be initiated, for example, by a user input via user interface 32, or may occur automatically when coupled to a charging station (not shown). For example, during the reset sequence controller 26 may execute program instructions to command drives 361, 362, 363 and 364 of electrical drive assembly 36 of electromechanical power source 28 of driver assembly 12 to the initialized state to preposition the mechanical components 401, 402, 403, and 404 of drives 361, 362, 363, and 364, respectively, of driver assembly 12 to correspond to the factory preset state of a new biopsy probe assembly 14, to thereby facilitate the proper mechanical drivable coupling between driver assembly 12 and biopsy probe assembly 14.

Likewise, successful installation of biopsy probe assembly 14 on an initialized driver assembly 12 will not occur unless, for example, the mechanical components 421, 422, 158, and 504 of biopsy probe assembly 14 are prepositioned in the proper initial positions to accommodate driving engagement with the coupling components of drives 361, 362, 363, and 364 of electrical drive assembly 36 of electromechanical power source 28 of driver assembly 12.

If, for example, one or more of cover 141, first driven unit 421 (linear cannula driver) of transmission device 42, or slider driver 504 of slider assembly 500 of biopsy probe assembly 14 has moved relative to housing 57 from the desired installation position prior to installation, then biopsy probe assembly 14 cannot be mounted to driver assembly 12 without further mechanical manipulation of biopsy probe assembly 14. In the absence of the following aspect of the present invention, such movement may occur, for example, during transport of biopsy probe assembly 14, during removal of biopsy probe assembly 14 from sterile packaging, or during the installation process.

Figure 20:
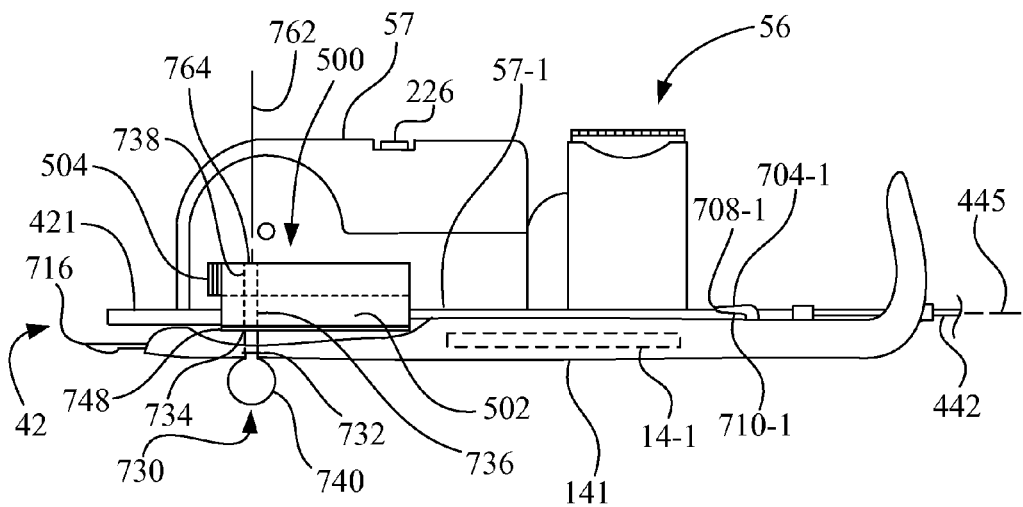
FIG. 20 is a side view of a portion of the biopsy probe assembly of FIG. 1, opposite to the side view shown in FIG. 2, and illustrating a slider assembly and the safety alignment pin installed.

Referring to FIG. 20, in accordance with an aspect of the present invention, a safety alignment pin 730 (sometimes referred to hereinafter as alignment pin 730) is installed in biopsy probe assembly 14 as an assembly step at some time prior to sealing biopsy probe assembly 14 in sterile packaging. The installation of safety alignment pin 730 in biopsy probe assembly 14 insures that the components of the new biopsy probe assembly 14 are prepositioned in the proper initial positions prior to and during installation of biopsy probe assembly 14 in driver assembly 12. For example, as more fully described below, alignment pin 730 is configured to facilitate concurrent engagement with each of the alignment features 732, 734, 736, and 738 in each of cover 141, housing 57, first driven unit 421 (e.g., a linear cannula driver) of transmission device 42, and slider assembly 500, respectively, so as to lock the relative positions of cover 141, housing 57, first driven unit 421 (e.g., linear cannula driver) of transmission device 42, and slider driver 504 of slider assembly 500, preferably until after housing 57 is seated in elongate cavity 241 of driver assembly 12.

In FIG. 20, a portion of cover 141 is shown cut away to fully expose alignment feature alignment feature 734 of housing 57. Also, alignment features 736 and 738 are represented by dashed lines.

Figure 21:
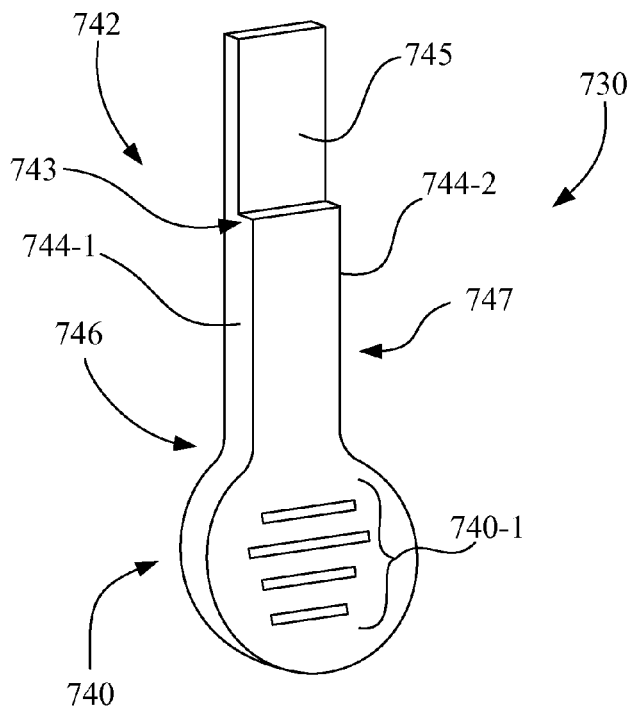
FIG. 21 is an enlarged perspective view of the safety alignment pin shown in FIG. 20.

Referring also to FIG. 21, alignment pin 730 has a head 740 and an elongate portion 742 that extends away from head 740. The head 740 has a set of grooves 740-1 positioned and configured to be grasped by a user, so as to aid in the manual manipulation of alignment pin 730. Grooves 740-1 may be present on opposing exterior sides of head 740. In the present embodiment, elongate portion 742 has generally a rectangular cross section 743, so as to provide abrupt engagement surfaces 744-1, 744-2. Elongate portion 742 has a thin notched portion 745 providing an offset to establish a correct orientation of alignment pin 730 relative to the respective alignment features. Also, a flared portion 746 at the junction of head 740 and elongate portion 742 serves to form an interference fit with alignment feature 732 of with cover 141 to aid in holding alignment pin 730 in position in biopsy probe assembly 14. Intermediate of flared portion 746 and thin notched portion 745 is a thick portion 747.

Referring also to FIG. 22A, cover 141 has alignment feature 732, which for example may be in the form of a slotted opening, sized and configured, e.g., as a rectangular slot, to slidably receive elongate portion 742 of alignment pin 730 in a snug fit.

Referring also to FIG. 22B, a protruding portion 748 of housing 57 adjacent to cover 141 has alignment feature 734, which for example may be in the form of a slot, sized and configured, e.g., as a rectangular slot, to slidably receive elongate portion 742 of alignment pin 730 in a snug fit.

Referring also to FIG. 22C, first driven unit (cannula driver) 421 is formed as an elongate slide 750 having a side wall 751, with alignment feature 736, which may for example be in the form of a channel 752 formed in side wall 751, that is sized and configured, i.e., as a rectangular channel, to slidably receive elongate portion 742 of alignment pin 730 in a snug fit.

Referring to FIGS. 22D and 22F, slider driver 504 of slider assembly 500 includes a side wall 754 into which alignment feature 738 is formed. Alignment feature 738 may be formed as a channel 756. Channel 756 is sized and configured, i.e., as a rectangular channel, to slidably receive thin notched portion 745 of elongate portion 742 of alignment pin 730 in a snug fit.

Referring also to FIGS. 22E and 22F, slider 506 includes a side wall 758 into which there is formed a guide channel 760. Guide channel 760 is positioned opposite to alignment feature 736 of first driven unit (cannula driver) 421. In conjunction, when alignment feature 736 of first driven unit (cannula driver) 421 is aligned with guide channel 760 of slider 506, thick portion 747 of alignment pin 730 is received therein.

As will be appreciated by those skilled in the art, when alignment feature 732 of cover 141, alignment feature 734 of housing 57, and alignment feature 736 of first driven unit 421, and alignment feature 738 of slider driver 504 are axially aligned along an alignment axis 762 (see FIG. 20), a continuous passage 764 (see FIG. 22A) is formed into which alignment pin 730 is manually inserted by a user so as to be concurrently positioned in, and engaged with, each of alignment features 732, 734, 736 and 738 so as to lock the relative positions of cover 141, housing 57, first driven unit 421 and slider driver 504. In the present exemplary embodiment, alignment axis 762 is arranged substantially orthogonal to, but not intersecting with, longitudinal axis 445. The locations of alignment feature 732 of cover 141, alignment feature 734 of housing 57, alignment feature 736 of first driven unit 421, and alignment feature 738 of slider driver 504 are selected such that when continuous passage 764 is formed and elongate portion 742 of alignment pin 730 is fully inserted into continuous passage 764, alignment pin 730 does not interfere with the seating of housing 57 in elongate cavity 241 of driver assembly 12 during installation.

However, during the installation of biopsy probe assembly 14 on driver assembly 12, even after the relevant portion (e.g., housing 57) of biopsy probe assembly 14 is seated in elongate cavity 241 of driver assembly 12, the mounting of biopsy probe assembly 14 to driver assembly 12 cannot be completed until alignment pin 730 is removed from biopsy probe assembly 14. The reason is that with alignment pin 730 concurrently engaged with the respective alignment features of the various movable components of biopsy probe assembly 14, e.g., alignment feature 732 of cover 141, alignment feature 734 of housing 57, alignment feature 736 of first driven unit 421, and alignment feature 738 of slider driver 506, the cover 141 cannot be slid relative to housing 57 to latch biopsy probe assembly 14 to driver assembly 12.

Thus, referring again to FIGS. 14-20 and 22A, to complete the mounting of biopsy probe assembly 14 to driver assembly 12, after seating the relevant portion, e.g., housing 57, of biopsy probe assembly 14 in elongate cavity 241 of driver assembly 12, alignment pin 730 is removed from continuous passage 764 of biopsy probe assembly 14 so as to permit cover 141 to be slid relative to housing 57 in direction 726, at which time cantilever rails 704-1, 704-2 of cover 141 are free to lockably engage the respective locking slots 714-1, 714-2 formed in housing 24 of driver assembly 12 and latch tab 716 of cover 141 is free to lockably engage tab slot 720 in housing 24 of driver assembly 12, to thereby latch biopsy probe assembly 14 to driver assembly 12.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy probe assembly configured for installation on a driver assembly, comprising:
   a biopsy probe having a sample basket arranged coaxially with a cutter cannula along a longitudinal axis;
   a cover having a first alignment feature;
   a housing slidably coupled to said cover, said housing having a second alignment feature;
   a cannula driver having a third alignment feature, said cannula driver being slidably coupled to said housing, said cannula driver connected to said cutter cannula to facilitate movement of said cutter cannula along said longitudinal axis;
   a flexible toothed rack connected to said sample basket to facilitate movement of said sample basket along said longitudinal axis;
   a gear train contained in said housing, said gear train including a clutch drive configured to selectively drivably couple said gear train to said flexible toothed rack;
   a pivot member pivotably coupled to said cannula driver, said pivot member providing selectable coupling between said cannula driver and said flexible toothed rack;
   a slider assembly coupled to said pivot member to operate said pivot member to facilitate said selectable coupling between said cannula driver and said flexible toothed rack via said pivot member, said slider assembly being further configured to selectively engage said clutch drive, said slider assembly including a slider driver movable between an extended position and a retracted position, said retracted position of said slider driver configured to effect engagement of said clutch drive and disengagement between said cannula driver and said flexible toothed drive, and said extended position of said slider driver effecting a disengagement of said clutch drive and an engagement between said cannula driver and said flexible toothed drive, said slider driver having a fourth alignment feature; and
   an alignment pin configured to facilitate manual concurrent engagement with each of said first alignment feature, said second alignment feature, said third alignment feature and said fourth alignment feature so as to lock relative positions of said cover, said housing, said cannula driver and said slider driver,
   wherein each of said first alignment feature, said second alignment feature, said third alignment feature, and said fourth alignment feature is one of a slot and a channel, and said alignment pin has an elongate portion with a rectangular cross section, with said elongate portion received by said first alignment feature, said second alignment feature, said third alignment feature, and said fourth alignment feature.

2. The biopsy probe assembly of claim 1, wherein when said alignment pin is concurrently engaged with said first alignment feature, said second alignment feature, said third alignment feature and said fourth alignment feature, said slider driver is in said retracted position.

3. The biopsy probe assembly of claim 1, wherein said concurrent engagement occurs when said first alignment feature, said second alignment feature, said third alignment feature and said fourth alignment feature are aligned to form a continuous passage, with said alignment pin received in said continuous passage.

4. The biopsy probe assembly of claim 3, configured such that when said continuous passage is formed, said slider driver is in said retracted position.

5. A method for installing a biopsy probe assembly on a driver assembly to form a biopsy apparatus, comprising:

prepositioning a drive of said driver assembly to an initialized state;

providing said biopsy probe assembly configured for installation on said driver assembly, said biopsy probe assembly including a biopsy probe having a cannula arranged along a longitudinal axis coaxially with a sample basket, a cover having a first alignment feature, a housing slidably coupled to said cover, said housing having a second alignment feature, and a first driven unit slidably coupled to said housing, said first driven unit having a third alignment feature, said first driven unit being connected to said cannula to facilitate movement of said cannula along said longitudinal axis, wherein said first alignment feature, said second alignment feature and said third alignment feature are aligned to form a continuous passage, with an alignment pin being received in said continuous passage to lock relative positions of said cover, said housing and said first driven unit;

seating at least a portion of said biopsy probe assembly in an elongate cavity of said driver assembly, with said drive drivably engaging said first driven unit;

after said seating, removing said alignment pin to unlock said cover, said housing, and said first driven unit; and after said alignment pin is removed, sliding said cover relative to said housing to latch said biopsy probe assembly to said driver assembly.

* * * * *